(12) United States Patent
Grevious et al.

(10) Patent No.: US 8,751,001 B2
(45) Date of Patent: Jun. 10, 2014

(54) UNIVERSAL RECHARGING OF AN IMPLANTABLE MEDICAL DEVICE

(75) Inventors: John J. Grevious, Minneapolis, MN (US); Todd A. Kallmyer, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 652 days.

(21) Appl. No.: 12/575,273

(22) Filed: Oct. 7, 2009

(65) Prior Publication Data
US 2010/0106223 A1 Apr. 29, 2010

Related U.S. Application Data

(60) Provisional application No. 61/107,761, filed on Oct. 23, 2008.

(51) Int. Cl.
*A61N 1/372* (2006.01)
*A61N 1/378* (2006.01)

(52) U.S. Cl.
USPC .............................................. 607/32; 607/60

(58) Field of Classification Search
USPC ........................................ 607/32–34, 59–65
See application file for complete search history.

(56) References Cited

U.S. PATENT DOCUMENTS

| | | | |
|---|---|---|---|
| 4,285,346 A * | 8/1981 | Armitage | ........................ 607/99 |
| 4,665,896 A | 5/1987 | Laforge et al. | |
| 5,117,825 A | 6/1992 | Grevious | |
| 5,562,714 A | 10/1996 | Grevious | |
| 5,683,432 A * | 11/1997 | Goedeke et al. | ................ 607/32 |
| 6,430,444 B1 | 8/2002 | Borza | |
| 6,885,353 B2 | 4/2005 | Kurihara | |
| 7,053,501 B1 | 5/2006 | Barrass | |
| 7,092,762 B1 | 8/2006 | Loftin et al. | |
| 7,167,756 B1 | 1/2007 | Torgerson et al. | |
| 7,211,986 B1 | 5/2007 | Flowerdew | |
| 2004/0098068 A1 | 5/2004 | Carbunaru et al. | |
| 2004/0266378 A1* | 12/2004 | Fukamachi et al. | ....... 455/188.1 |
| 2005/0212714 A1* | 9/2005 | Chiang et al. | ................. 343/810 |
| 2006/0246846 A1 | 11/2006 | Ginggen et al. | |
| 2009/0118796 A1 | 5/2009 | Chen et al. | |

OTHER PUBLICATIONS

"Smoothing Capacitors." REUK. <http://www.reuk.co.uk/Smoothing-Capacitors.htm>. Apr. 4, 2001. Web. Dec. 3, 2012.*
Partial International Search Report dated Feb. 10, 2010.
PCT International Search Report and Written Opinion dated Feb. 16, 2011.
PCT Search Report and Written Opinion dated Feb. 16, 2011.

* cited by examiner

*Primary Examiner* — Allen Porter, Jr.
(74) *Attorney, Agent, or Firm* — Beth L. McMahon; Medtronic, Inc.

(57) ABSTRACT

Techniques associated with a universal recharging device for recharging a power source of implantable medical devices (IMDs). The recharging device includes an interface to allow an antenna assembly to be removably coupled. The antenna assembly has a primary coil and a corresponding sense coil. The sense coil has a configuration that is selected based on the configuration of the primary coil. The sense coil is adapted to prevent voltage across the primary coil from exceeding a maximum voltage amplitude allowable with the recharging device. The maximum voltage amplitude may be selected based on a maximum magnetic field strength to which a patient is to be exposed. In one embodiment, the maximum voltage amplitude is programmable.

57 Claims, 9 Drawing Sheets

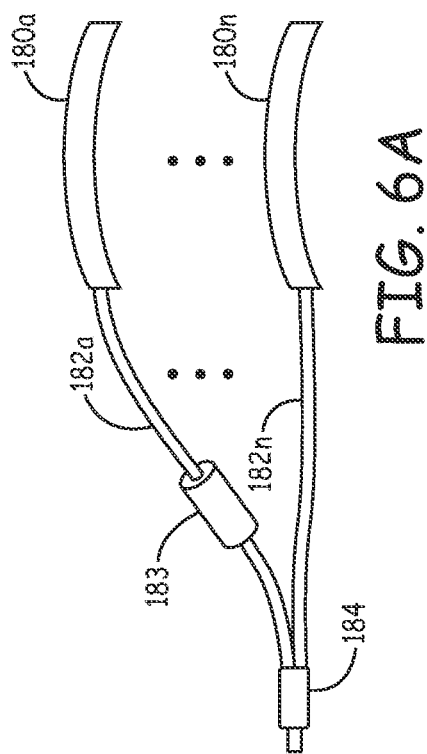
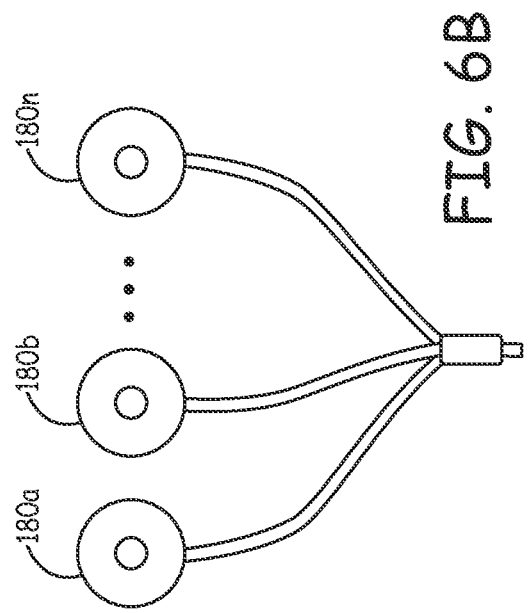
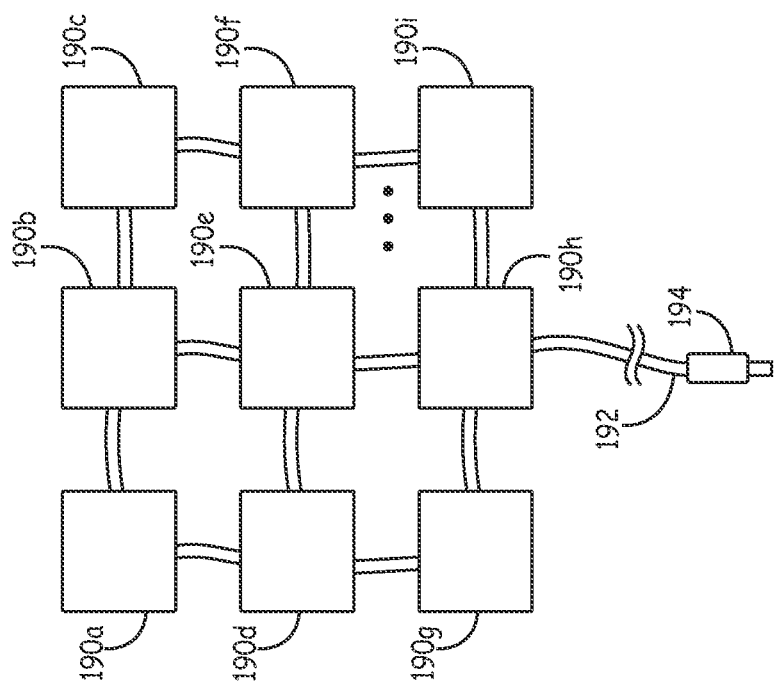

UNIVERSAL RECHARGING OF AN IMPLANTABLE MEDICAL DEVICE

RELATED APPLICATIONS

This application claims priority to provisionally-filed patent application Ser. No. 61/107,761 filed on Oct. 23, 2008 entitled "Universal Recharger for an Implantable Medical Device", which is incorporated herein by reference in its entirety.

FIELD OF THE INVENTION

This invention relates to implantable medical devices and, in particular, to energy transfer devices, systems and methods for implantable medical devices.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Of course, it is recognized that other implantable medical devices are envisioned which utilize energy delivered or transferred from an external device.

A common element in all of these implantable medical devices is the need for electrical power in the implanted medical device. The implanted medical device requires electrical power to perform its therapeutic function, which may include driving an electrical infusion pump, providing an electrical neurostimulation pulse or providing an electrical cardiac stimulation pulse. This electrical power is derived from a power source.

In some implantable medical devices electrical power can be transcutaneously transferred through the use of inductive coupling. For instance, this can be accomplished by inductively coupling a primary coil that is external to a living body with a secondary coil that is coupled to, or included within, the implantable medical device. Current induced in the secondary coil is used to store energy in a rechargeable battery and/or to power the implantable medical device implanted within the body. In this form, an internal power source, such s a battery, can be used for direct electrical power to the implanted medical device. When the battery has expended, or nearly expended, its capacity, the battery can be again recharged transcutaneously, via inductive coupling from an external power source that drives the primary coil, which is temporarily positioned on the surface of the skin.

Many devices and techniques have been developed to provide transcutaneous energy transfer in order to power an implantable medical device and/or charge or recharge a battery associated with an implantable medical device. As previously noted, techniques generally employ a primary coil driven by an external power source.

BRIEF SUMMARY OF THE INVENTION

A universal recharging device for recharging a power source of implantable medical devices (IMDs) is disclosed. The recharging device includes a connector that may be removably coupled to a recharge antenna assembly that may be any one of multiple configurations. As used herein, antenna configuration refers to the physical characteristics (e.g., size, shape, area, number of coil turns, etc.) and electrical and magnetic characteristics (e.g., inductance) of a primary recharge coil housed within the antenna assembly, and which is used to inductively couple to a secondary coil of an IMD to recharge a power source of the IMD.

A given recharge antenna assembly that may be removably coupled to the recharging device will have a configuration that is adapted for use with a particular implant scenario. As used herein, "implant scenario" refers to all of the factors that will determine, or affect, how a secondary coil of the IMD will couple to a primary coil of the antenna assembly, including, but not limited to, IMD type, IMD model, implant depth, implant location in a body, implant orientation, and physical, electrical, and magnetic characteristics of the secondary coil of the IMD (e.g., number of turns, size, shape, area, etc.). For instance, the size, shape, area, and number of turns of a primary coil within the recharge antenna assembly will be selected to generate a magnetic field having a strength that is appropriate for the implant scenario, as may be determined by implant depth and the coil of the particular IMD that is involved in the recharge operation.

According to the disclosure, a recharge antenna assembly further includes a corresponding sense coil. The sense coil is positioned to be inductively coupled to the primary coil of the antenna assembly when the antenna is being used to recharge the power source of the IMD. The configuration of the sense coil (e.g., physical, electrical, and magnetic characteristics) is selected so that when the primary and sense coils are inductively coupled, a given ratio will be maintained between the amplitude of the voltage across the sense coil and the amplitude of the voltage across the primary coil. A voltage limiting circuit is provided to limit the maximum voltage amplitude across the sense coil during recharge of the rechargeable power source. This limits the voltage amplitude across the primary coil based on the selected ratio.

The maximum voltage that is to be allowed across the primary coil (as is determined by the maximum allowed voltage selected for use with the sense coil) may be chosen based on electrical characteristics of the recharging device and/or characteristics of the antenna assembly interface. Additionally or alternatively, the maximum allowable voltage selected for use with the primary coil may be based on a desired maximum magnetic field strength that is to be associated with the antenna assembly, and/or to which a patient is to be subjected. Other considerations may be used to select the maximum allowable voltage amplitude across the primary coil.

In one embodiment, the voltage limiting circuit is programmable such that the maximum voltage amplitude across the sense coil is programmably selectable. According to another aspect, while the voltage limiting circuit is limiting voltage across the sense coil to a selected maximum voltage amplitude, energy is being removed from the antenna assembly. This energy is transferred to recharge a power source of the recharging device. Another aspect relates to limiting the amount of energy transferred to the primary coil when the voltage across the sense coil reaches a selected maximum voltage amplitude.

Another aspect of the disclosure allows multiple antenna assemblies, any of which may have a different configuration from another antenna assembly, to be physically coupled to a recharging device at once. At any given time, one or more of these antenna assemblies may be selectably enabled for use in recharging a power source of the IMD. The enabling of the one or more antenna assemblies may be performed automatically using identification information that may be read from a given antenna assembly using encoded signals transferred between the recharging device and the IMD coils.

The recharging device of the current disclosure may include a tuning oscillator for use in manually or automatically tuning recharging to the resonant frequency of an antenna assembly when the antenna assembly is recharging the power source of the IMD. The recharging device may further contain a circuit to determine a resonant frequency of a communication of the IMD, this frequency being used to perform uplink and downlink communication sessions between recharging device and the IMD.

According to one aspect, a system is disclosed that comprises a device adapted to charge a rechargeable power source of an IMD and an antenna assembly removably coupled to the device. The antenna assembly has a primary coil and a corresponding sense coil, the sense coil having a configuration that is selected based on the configuration of the primary coil. The sense coil is adapted to prevent voltage across the primary coil from exceeding a maximum voltage amplitude allowable for use with the device.

Another aspect relates to a system that is adapted to recharge a rechargeable power supply of an IMD. The system comprises a primary coil interface adapted to be removably coupled to a primary coil that may any selected one of multiple coil configurations. The system further comprises a sense coil interface adapted to be removably coupled to a sense coil and to regulate voltage amplitude across the sense coil while the primary coil interface is being used to recharge the rechargeable power supply, thereby limiting voltage amplitude across the primary coil interface to a maximum voltage amplitude allowable on the primary coil interface.

Another aspect relates to an antenna assembly for use in recharging an IMD having a secondary coil. The antenna assembly comprises a primary coil and a sense coil. A sense coil interface is coupled to the sense coil and is adapted to limit strength of a magnetic field that couples the primary coil to the sense coil when the primary coil is inductively coupled to the secondary coil.

A method of recharging a rechargeable power source of an implantable medical device is further disclosed. The method includes providing a recharging device and providing an antenna assembly adapted to be removably coupled to the recharging device. The antenna assembly includes a primary coil that may be any one of multiple types of primary coils. The method further includes providing the antenna assembly with a sense coil configured to maintain a given ratio between voltage across the primary coil and voltage across the sense coil when the antenna assembly is recharging the rechargeable power source.

Yet another aspect relates to a system including an IMD and an external device adapted to transmit electromagnetic energy to the IMD. An antenna assembly is removably coupled to the external device. The antenna assembly has a primary coil and a corresponding sense coil. The sense coil has a configuration that is selected based on the configuration of the primary coil, the sense coil being adapted to prevent voltage across the primary coil from exceeding a maximum voltage amplitude allowable for use with the external device.

Other aspects will become apparent from the following description and the accompanying drawings.

BRIEF DESCRIPTION OF THE DRAWINGS

FIG. 6A is a side view of a multi-antenna array.

FIG. 6B is a top view of the multi-antenna array of FIG. 6A.

FIG. 6C is a top view of a two-dimensional multi-antenna array.

DETAILED DESCRIPTION OF THE INVENTION

Techniques are disclosed for supporting interchangeability between one or more primary coils that are coupled to an external power source that is used to recharge and/or power an implantable medical device (IMD). IMDs have varying types of secondary coil and rechargeable power source designs, each having different types of requirements. For instance, the size, shape, and/or orientation of the secondary coil within a particular IMD, and/or the likely implant depth of the IMD based on therapy requirements may vary according to IMD type. As a result, it is often necessary to use a specific primary coil design to recharge a given type of IMD. This, in turn, has previously required the use of a specific type of external power source that has been designed to adapt to, and operate with, the design of the primary coils.

The innovative techniques described herein eliminate the requirement to provide a different, unique power source design for each coil configuration, as was necessary in the past. Because the disclosed techniques allow a single power source to be used to drive virtually any type, form factor, and configuration of primary coil, only one power source design need be engineered, tested, manufactured, stocked, marketed, and distributed. The resulting cost savings are very significant for the manufacturer of the external power system. The cost savings are also significant for health-care providers and users, which in the past were required to purchase a different power source for each type of primary coil design that was needed to recharge a given type of IMD. This expense is eliminated in favor of a single power source that may be "mixed and matched" with various primary coil designs.

The techniques described herein further provide simplification for a user, such as a patient or clinician, who now is only required to become familiar with this single model of power supply. This is particularly important in the case of a clinician, who, in the past, may have been required to become familiar with many different styles and models of power sources, each of which was specifically designed to power a different type of primary coil.

Yet another benefit relates to space savings, since a clinic, hospital, or other health care facility need only provide shelf space for a single power source. This is significant in small physician offices, wherein storage space provided for storing medical equipment may be at a premium. This is also significant for a patient who has been implanted with multiple types of IMDs, since the patient no longer needs to store, maintain, and travel with multiple types of power sources in support of those various medical devices.

Before describing the specifics of the above-described techniques in more detail, a discussion of an exemplary IMD that may be employed with such techniques is provided.

Figure 1:
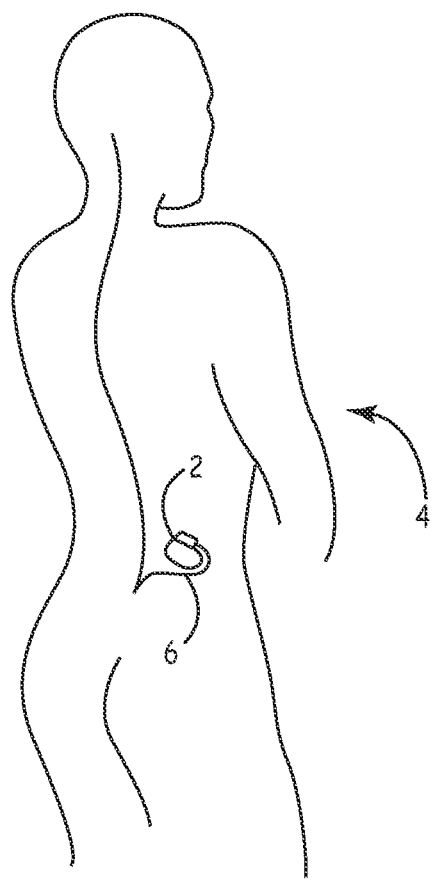
FIG. 1 is a diagram illustrating an exemplary Implantable Medical Device, which may be a neurostimulator, implanted in patient.

FIG. 1 shows an exemplary IMD 2. IMD may be adapted to deliver a type of therapy to the patient, which may include electrical stimulation and/or drug therapy to a patient. Many types of implantable medical devices may utilize the disclosed recharging systems and techniques, including implantable therapeutic substance delivery devices, implantable drug pumps, cardiac pacemakers, cardioverters or defibrillators, devices to deliver electrical stimulation pulses for a neurological or muscular condition, devices to deliver electrical stimulation to alleviate pain, or any other IMDs for delivering therapy. Such therapy may be delivered via one or more therapy connections 6, which may be one or more leads and/or catheters. The patient's body may carry additional IMDs which may be similar to, or different from, IMD 2.

Figure 2:
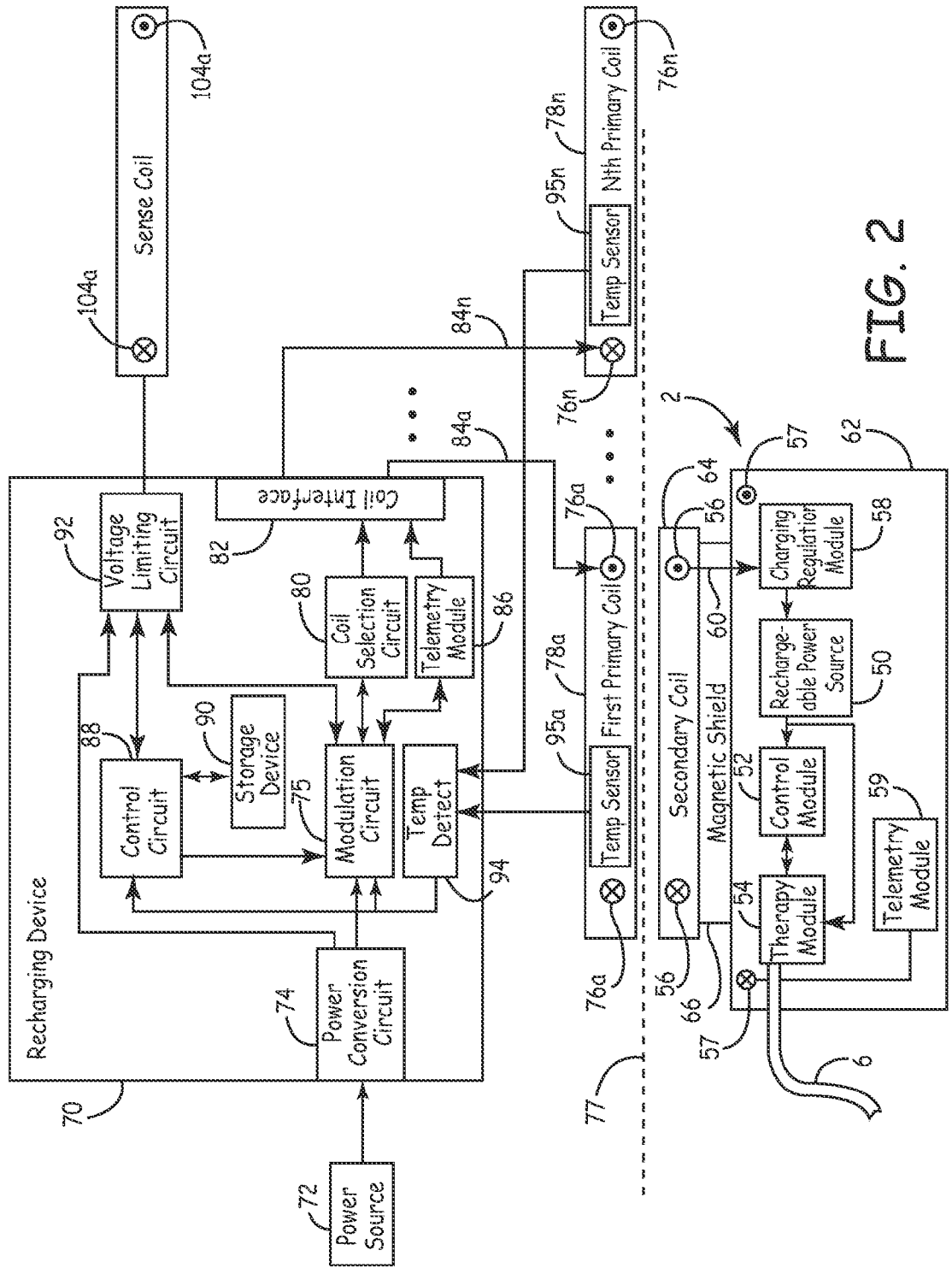
FIG. 2 is a block diagram of one embodiment of the Implantable Medical Device (IMD) of FIG. 1 and a recharging device for recharging a power source of the IMD.

FIG. 2 is a block diagram of one embodiment of IMD 2 and recharging device for recharging a power source 50 within the IMD. According to the current disclosure, IMD 2 includes a rechargeable power source 50. Rechargeable power source 50 can be any of a variety of rechargeable power sources including a chemically-based battery or a capacitor. In one embodiment, rechargeable power source 50 is a lithium ion battery. Any other type of rechargeable battery suitable for powering an IMD may be used.

Rechargeable power source 50 is coupled to a control module 52, which includes circuitry to control therapy delivered to the patient. Control module 52 may include one or more microprocessors, application-specific integrated circuits (ASICs), digital signal processors (DSPs), field-programmable gate arrays (FPGAs), discrete electronic components, state machines, sensors, and/or other circuitry.

Control module 52 is further coupled, and provides power, to therapy module 54. Therapy module 54 delivers some form of therapy to a patient. This therapy may include controlled delivery of a substance and/or electrical stimulation. For example, in one embodiment, therapy module 54 may include one or more output pulse generators such as capacitive elements, voltage regulators, current regulators, voltage sources, current sources, and/or switches that are coupled to rechargeable power source 50 directly or through control circuit 52. Therapy module 54 may deliver electrical pulses to patient 4 via a combination of electrodes. Therapy module 54 is coupled to patient 2 through one or more therapy connections 6 such as leads and/or catheters.

In one embodiment, rechargeable power source 50 is coupled to a secondary coil 56 (shown in cross-section) through a charging regulation module 58. During a recharge session, a current is induced in secondary coil 56 in a manner to be discussed below. This current is provided via connection 60 to charging regulation module 58, which controls the charging of rechargeable power source 50.

IMD 2 may also include a telemetry module 59 coupled to a telemetry coil 57 (shown in cross-section). Telemetry coil 57 and telemetry module 59 may utilize various types of telemetry protocols to communicate with external recharging device 70. A proximity telemetry system is utilized for telemetry distances of 5 centimeters or less. An arm's length telemetry system is employed for distances of up to 1 meter. This latter type of system may utilize the electric field (E-field) component of a propagating wave to transmit information (e.g., the MICS band set aside for medical device telemetry.) Arm's length telemetry may also be achieved using the magnetic (H-field) component or coupled-coil transmission.

Rechargeable power source 50, charging regulation module 58, control circuit 52, therapy module 54, telemetry module 59 and telemetry coil 57 may be contained in a hermetically sealed housing 62. Secondary coil 56 may be attached to, or positioned on, an exterior surface of sealed housing 62 through connection 60. For instance, secondary coil 56 may be contained within a second housing 64 that is positioned adjacent to sealed housing 62. In an alternative embodiment, secondary coil 56 may be contained in housing 62 along with the other electronics.

In one embodiment, a magnetic shield 66 may be positioned between secondary coil 56 and housing 62. The primary purpose of magnetic shield 66 is to substantially increase the amount of energy captured by the secondary coil. Magnetic shield 66 also protects rechargeable power source 50, control circuit 52, therapy module 54 and charging regulation module 58 from electromagnetic energy when secondary coil 56 is utilized to charge rechargeable power source 50.

FIG. 2 further illustrates one embodiment of a recharging device 70 for recharging rechargeable power source 50. Recharging device 70 is coupled to a power source 72, which may be a source of AC power, such as a standard wall outlet. In another embodiment, power source 72 may include one or more batteries, thereby allowing recharging device to be portable so that a patient may recharge rechargeable power source 50 of IMD 2 while going about a daily routine. For instance, in this case, power source 72 may include Li+ rechargeable batteries. Li+ batteries can be packaged in thin, flexible foil packs. Such batteries would have to be recharged, as by placing the batteries, or in some embodiments, the entire recharging device 70, in a recharge cradle or some other recharging device. In other embodiments, the batteries may be non-rechargeable batteries.

Power received from power source 72 such as a wall outlet or a battery may be received in one embodiment by power conversion circuit 74, which supplies appropriate power to modulation circuit 75. Modulation circuit 75 is a frequency generator to generate a recharge signal, typically somewhere between 8 kilohertz and 500 kilohertz. The recharge signal may be a sine wave or some other type of signal, if desired. The frequency of the recharge signal may depend on the resonant frequency of the system, which takes into account the loading placed on the system when secondary coil 56 is inductively coupled across cutaneous boundary 77 (shown dashed) to one or more primary coils 76a-76n (hereinafter, "primary coils 76") that are housed in antenna assemblies 78a-78n (hereinafter, "antennas 78"), respectively. Recharging device 70 may vary the frequency during a charging session to find the most optimal frequency for charging efficiency.

The signal generated by modulation circuit 75 is provided to coil selection circuit 80 which drives primary coils 76 through coil interface 82 via interconnections 84a-84n, which may be cables. Primary coils 76 may be of many different configurations (e.g., shapes, sizes, and including any number of turns). The configuration of primary coils 76 will generally be selected based on the size and shape of secondary coil 56, as well as the implant scenario associated with IMD 2. For instance, if IMD 2 is intended for use in a deep implant scenario, it may be desirable to configure primary coils 76 to include a large number of coil turns, since this will result in the generation of a larger magnetic field, which will be needed to achieve adequate inductive coupling at the greater implant depth. This may likewise be true if primary coils 76 are intended for placement at some distance from cutaneous boundary 77 instead of directly on cutaneous boundary, as may be applicable for some implant scenarios, such as when an insulator or a cooling device is positioned between the primary coils 76 and the cutaneous boundary.

In one embodiment, recharging device is coupled to a single primary coil 76. In another embodiment wherein recharging device is coupled to more than one primary coil 76, recharging device is capable of driving some, or all, of the primary coils 76 at the same time so that a current is produced in each of the coils. As one example, multiple primary coils 76 may be driven with the same amplitude, frequency, and phase. As another example, multiple coils may have varying amplitudes but a same frequency and phase. This is discussed further below.

Recharging device 70 may have a telemetry module 86 enabling recharging device 70 to be in communication with IMD 2 during a charging session, as may be desirable to provide status concerning the charging session. Telemetry module 86 may be adapted to utilize various types of telemetry protocols, including a proximity protocol for telemetry distances of 5 centimeters or less or an arm's-length telemetry protocol for distances of up to 1 meter.

In some embodiments, it may not be possible to deliver recharge energy while communicating with IMD 2 via a telemetry session. For instance, in the illustrated embodiment, telemetry module 86 is not coupled to a dedicated telemetry coil, but rather is coupled via coil interface 82 to one or more primary coils 76 that are used to both facilitate communication and to accomplish recharge. In such embodiments, recharging device 70 may temporarily stop transmitting recharge energy in order to poll IMD 2 for information. Recharge will remain inactivated until the telemetry session has completed. During this communication session, IMD 2 may communicate information to recharging device 70 that includes, for example, battery status. Such status may allow recharging device 70 to stop charging when the battery of IMD 2 has been fully recharged.

In another embodiment, recharging device 70 may be automatically activated using a telemetry signal received from IMD 2. For instance, recharging device 70 may continuously send out requests via telemetry communication. When IMD 70 is in proximity to rechargeable power source 50, IMD 2 sends an acknowledgement so that recharging device 70 may initiate a recharge session.

Operation of IMD 2 may be controlled by control circuit 88, which may include one or more microprocessors, FPGAs, ASICs, DSPs, microsequencers, discrete components, and/or other electronic circuit components. Control circuit 88 may provide control signals to indicate how modulation circuit 75 is to drive primary coils 78, for instance. In an embodiment wherein control circuit 88 operates according to programmed instructions (e.g., control circuit 88 includes a microprocessor), control circuit 88 is coupled to one or more storage devices 90. Storage device(s) 90 may include volatile, non-volatile, magnetic, optical, and/or electrical media for storing digital data and programmed instructions, including random access memory (RAM), read-only memory (ROM), non-volatile RAM (NVRAM), electrically erasable programmable ROM (EEPROM), flash memory, removable storage devices, and the like.

Recharging device 70 further includes a voltage limiting circuit 92. In one embodiment, this circuit operates in conjunction with one or more sense coils (shown as sense coil 104a in FIG. 2) to limit voltage levels on interfaces 84a-84n, as will be discussed below. Voltage limiting circuit 92 may also provide a signal to modulation circuit 75 to allow modulation circuit to drive the system with an input signal that will allow optimal energy transfer to occur to rechargeable power source 50.

In one embodiment, recharging device 70 may include a temperature detection ("temp detect") circuit 94. This circuit receives one or more signals from one or more of primary coils 76. For instance, a temperature sensor 95a included in first antenna 78a provides one or more signals via interface 96a to temperature detection circuit 94. Similar signals are provided by temperature sensor 95n of any other antennas 78. These signals are processed to determine if one or more of primary coils 76 housed by the antennas are exceeding acceptable temperature limits. Such limits may be based on government regulations, patient preferences, and/or some other standard. If the temperature of a sensor is exceeding a limit, temperature detection circuit 94 will provide a signal to control circuit 88. This will cause control circuit 88 to alter the signal driving the antenna 78 that is associated with the exceeded temperature limit so that the temperature of the antenna will be reduced to within acceptable limits.

Many alternative configurations are possible for both IMD 2 and recharging device 70. As already discussed, although an embodiment having multiple primary coils 76 is shown in FIG. 2, it is understood that the system may be limited to including a single primary coil. As another example, various logical functions of IMD 2 and/or recharging device 70 may be partitioned differently. For instance, control circuit 52 and therapy module 54 of IMD 2 may be combined into a single logic block, or into more logic blocks than are shown with respect to the current implementation. As will be discussed below, a sense coil and a primary coil may be included within a single antenna assembly, such as within antenna assembly 78n. Thus, the examples shown in FIG. 2 are to be considered illustrative in nature only.

As discussed above, recharging device 70 and the one or more primary coils 76 may be configured to optimally recharge IMD 2. For instance, primary coils 76 are generally selected to be of a similar size and shape as secondary coil 56. This will result in better inductive coupling between coils, which will, in turn, result in better energy transfer to the rechargeable power source 50. As another example, the number of turns in the primary coils 76 may be selected based on the likely implant depth and orientation of the IMD within a patient. For instance, if IMD 2 will likely be employed in an implant scenario involving a deep or angled implant, or if the coils are to be retained at some distance from cutaneous boundary 77 during recharge, it may be desirable to utilize primary coils 76 having an increased number of turns, which, in turn, will increase the magnetic field produced by these coils when the coils are driven with a given input signal. This increases magnetic field strength, as may be necessary to achieve adequate inductive coupling between the one or more primary coils 76 and the secondary coil 56 in these types of situations.

Changing the size and shape of the primary coils 76 affects the voltage amplitude generated across the coils. For a primary coil having N turns and an area A, a voltage across the coil is related to the strength of the magnetic field that is coupling the coil, $B_{coil}$ according to the following equation:

$$V_{coil} = NA2\pi f B_{coil} \qquad \text{Equation 1}$$

Thus, coil configuration (e.g., size, shape, and number of coil turns) greatly impacts voltage amplitude across the coil when the coil is driven by a predetermined input signal that generates a predetermined magnetic field, $B_{coil}$.

The configuration of the primary coils 76 will also affect the resonant frequency of the system when primary coils 76 are inductively coupled with a secondary coil 56. This is important since, to achieve optimal energy transfer between recharging device 70 and IMD 2, it is generally desirable to drive each primary coil 76 at the resonant frequency of the system.

To accommodate the various types of coil designs and the considerations discussed above, it has heretofore been desirable to tailor the design of recharging device 70 according to the type and design of the IMD with which it will be used. That is, each IMD will be associated with particulars such as a design of a secondary coil, a likely implant depth, a likely coil orientation, and so on. This, in turn, will determine the design of the one or more primary coils to be used to recharge the particular IMD. This primary coil design will then dictate the electrical characteristics of recharging device 70. Specifically, recharging device 70 may be designed to handle a predetermined maximum voltage at coil interface 82 that corresponds with the maximum coil voltage and/or coil current that will result when a primary coil 76 is driven by modulation circuit 75 with a predetermined input signal. The input signal will be selected to be within a frequency range that will correspond to the resonant frequency of the system when primary coils 76 are inductively coupled to secondary coil 56 of the IMD 2. Moreover, the input signal may be selected to generate no more than a maximum magnetic field strength at the primary coils 76 that limits exposure of the patient to the magnetic field.

The requirement to provide a specific recharging device 70 that corresponds to an associated primary coil design results in disadvantages. First, each model of the recharging device 70 must be designed, tested, approved for use by applicable government agencies, manufactured, stocked, and distributed. Moreover, a customer (e.g., clinician and/or patient) is required to purchase, maintain, and become familiar with, a different model of recharging device for each type of implant device the customer will be required to recharge.

To address the foregoing, the innovative techniques described herein eliminate the requirement to provide a unique design for recharging device 70 for each primary coil configuration, as was necessary in the past. Because the disclosed techniques allow a single universal recharging device 70 to be used to drive virtually any type, form factor, and configuration of primary coil, only one recharging device need be engineered, tested, approved by applicable regulatory agencies, manufactured, stocked, marketed, distributed, and purchased by customers. The resulting cost savings are very significant for both the designer/manufacturer of the recharging device and the user of this device.

According to one embodiment, one or more sense coils, depicted as sense coil 104a in FIG. 2, are used in conjunction with the one or more primary coils to limit the maximum voltage across each primary coil. By limiting the voltage across all primary coils to a same amplitude regardless of coil configuration, various primary coil designs may be employed with a given recharging device 70. Moreover, in one embodiment, an oscillator circuit, which may be a self-tuning oscillator, may be employed by recharging device 70 to tune the frequency at which the loaded primary coils 76 are driven to the resonant frequency of the system. If the tuning oscillator is self-tuning, this selection of the resonant frequency will occur automatically using a feedback signal. This will be discussed in reference to the remaining drawings.

Figure 3:
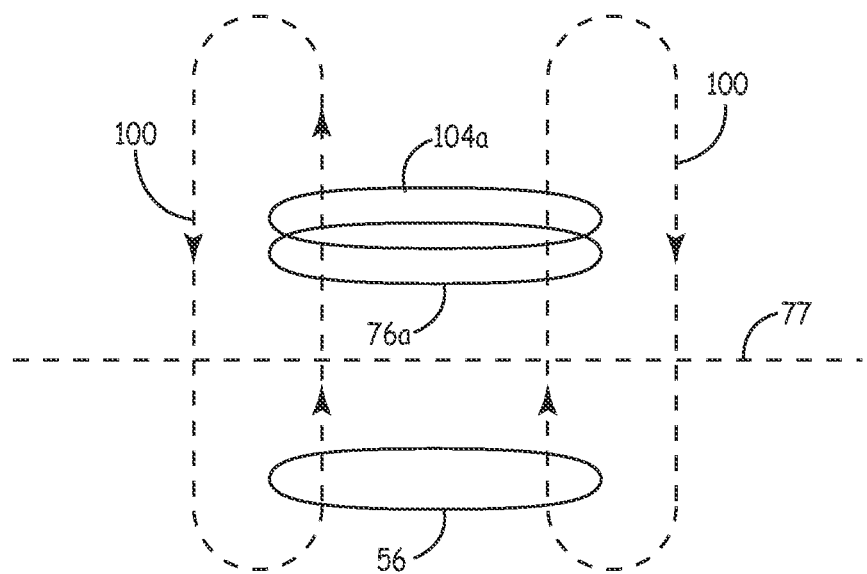
FIG. 3 is a flux diagram including a primary coil and sense coil of a recharging device and a secondary coil of an Implantable Medical Device.

FIG. 3 is a flux diagram including primary coil 76a and secondary coil 56 (FIG. 2). As is known in the art, an alternating current having a frequency f that is generated in a primary coil 76a induces a magnetic field represented by flux lines 100. The magnetic field, in turn, results in an alternating current in a secondary coil 56, which is shown located at the other side of cutaneous boundary 77 (shown dashed) when IMD 2 is implanted in a patient.

An alternating voltage is generated across both primary coil 76a and secondary coil 56 while the primary coil is being driven at the frequency f. As previously discussed, for a coil having N turns and an area A, a voltage across the coil is related to the strength of the magnetic field that is coupling the coil, $B_{coil}$, according to Equation 1 set forth above.

According to one aspect, a sense coil 104a may be positioned in close proximity to the primary coil 76a. When so positioned, the density of the flux lines 100 that pass through primary coil 76a matches that of the density of flux passing through sense coil 104a such that the magnetic field strength at both coils, $B_{coil}$, is approximately the same.

In view of the foregoing, one way to limit maximum voltage, $V_{max}$, at primary coil 76a to some predetermined amplitude is to "clamp" the voltage across the sense coil 104a to some corresponding maximum voltage $V_{max\_sense}$. This limits the maximum magnetic field strength, $B_{max\_sense}$ at both the sense coil 104a and primary coil 76a. This, in turn, prevents voltage across primary coil 76a from rising above a desired maximum voltage that is selected for use with a universal recharging device 70. This allows coil interface 82, modulation circuit 75, and the associated circuitry to be adapted for use with any coil configuration.

In one embodiment, voltage limiting circuit 92 (FIG. 2) may be used to facilitate the clamping of the voltage across sense coil 104a. Voltage limiting circuit 92 may be coupled to sense coil 104a to clamp the voltage of the sense coil to some selected voltage $V_{max\_sense}$ that may be programmable. This regulates $B_{max\_sense}$ to a programmable value determined by the equation $$B_{max\_sense} = V_{max\_sense}/(N_{sense}A_{sense}2\pi f) \qquad \text{Equation 2}$$

This, in turn, regulates the magnetic field strength at the primary coil 76a to some selectable value, and clamps the voltage across the primary coil.

Figure 4:
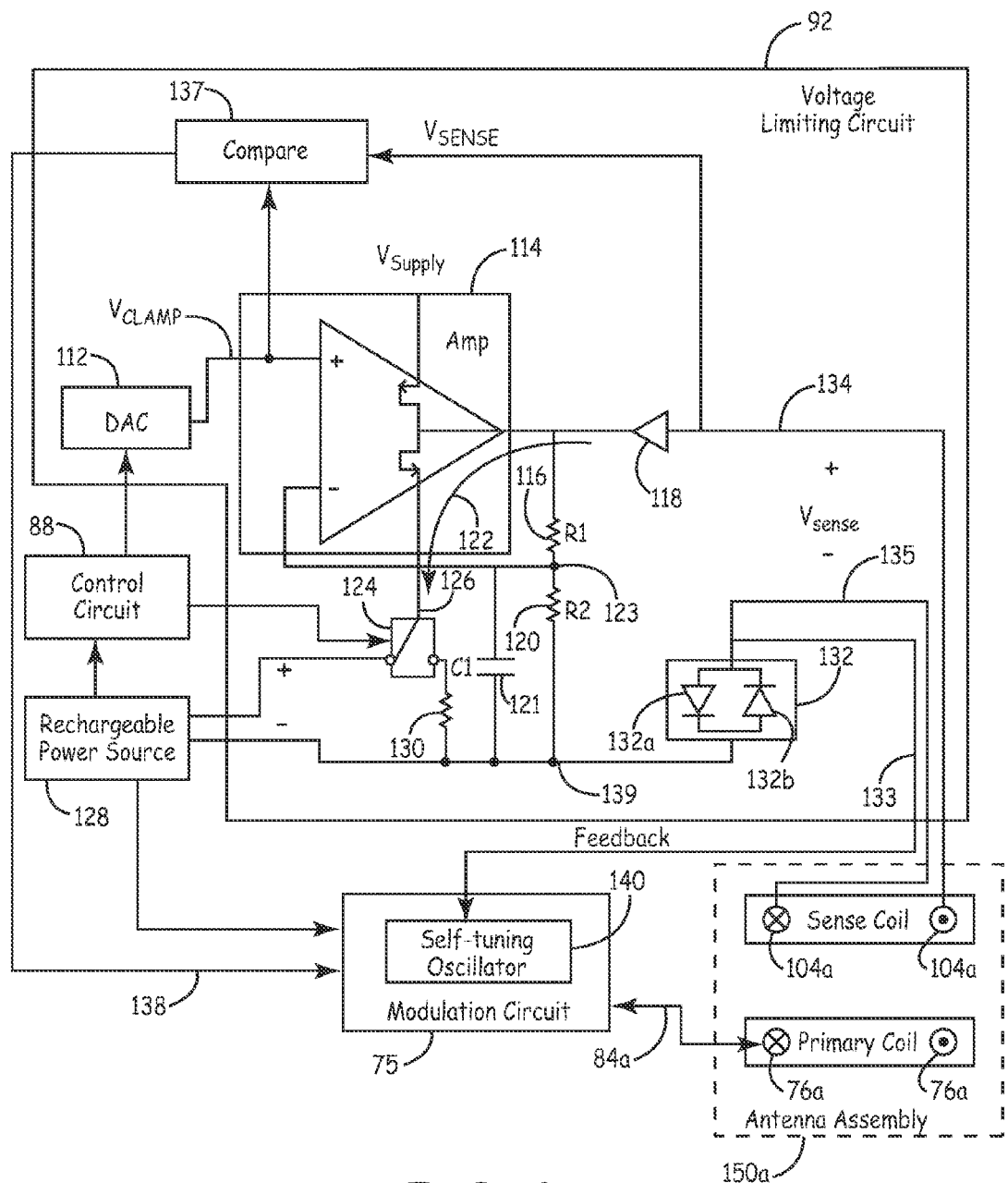
FIG. 4 is a block diagram of one embodiment of the voltage limiting circuit of FIG. 2.

FIG. 4 is a block diagram of one embodiment of voltage limiting circuit 92 and modulation circuit 75 of FIG. 2. For clarity, some of the interconnections and logic blocks shown in FIG. 2 are omitted. However, it will be understood that voltage limiting circuit 92 and modulation circuit 75 may be employed within a recharging device having a configuration that is similar to that shown in FIG. 2.

Voltage limiting circuit 92 of one embodiment is coupled to control circuit 88, which provides a selected digital value to a Digital-to-Analog Converter (DAC) 112 that selects a clamp voltage, $V_{clamp}$. DAC 112 supplies this analog voltage level $V_{clamp}$ to a positive input of differential amplifier 114. The negative input of this differential amplifier is connected through a resistor R1, 116, and a diode 118 to sense coil 104a.

During a recharge session, modulation circuit 75 drives a primary coil 76a via interface 84a, as may be accomplished via coil selection circuit 80 and coil interface 82 in one embodiment. This causes primary coil 76a to be inductively coupled to secondary coil 56 of IMD 2 (FIG. 2). This further causes primary coil 76a to be inductively coupled to sense coil 104a which is, in the illustrated embodiment, housed within a same antenna assembly 150a as the primary coil 76a. The inductive coupling of primary coil 76a to sense coil 104a results in an increase in the voltage across the sense coil.

As voltage across sense coil 104a increases, an increased current flowing through diode 118 and through resistors R1, 116, and R2, 120, causes the voltage amplitude across capacitor C1 121 to rise. When the voltage at node 123 increases beyond the clamping voltage $V_{clamp}$, amplifier 114 begins to limit the voltage at the output of diode 118 so that the voltage can no longer increase. In the exemplary embodiment, voltage at the positive terminal of the diode 118 (and hence across sense coil 104a) will thereby also be limited to $V_{max\_sense}$ as follows:

$$V_{max\_sense} = V_{clamp}(1 + R1/R2) + V_{diode} \quad \text{Equation 3}$$

In Equation 3, $V_{diode}$ is the voltage drop across diode 118 when that component is forward biased and the voltage at node 123 is approximately equal to $V_{clamp}$. R1 and R2 are the resistance values selected for resistors 116 and 120, respectively.

At the time limiting of voltage across sense coil 104a begins, current begins to flow through amplifier 114 in the direction of arrow 122. This removes energy from the system, thereby limiting voltage across primary coil 76a to a maximum voltage $V_{max\_primary}$ corresponding to $V_{max\_sense}$.

Preferably, the shape and size of sense coil 104a is selected to provide an accurate sample of the flux in primary coil 76a. Further, the primary coil 76a will preferably be positioned in close proximity to the sense coil 104a. When these conditions are met, $B_{sense} = B_{primary}$. Referring to Equation 2 above, this results in the following relationship:

$$V_{sense}(N_{sense}A_{sense}2\pi f) = V_{primary}/(N_{primary}A_{primary}2\pi f) \quad \text{Equation 4}$$

wherein $N_{primary}$ and $A_{primary}$ refers to the number of turns and area, respectively, of the primary coil.

In an embodiment wherein both coils are of a similar shape and size such that the area of sense coil 104a approximates that of the primary coil 76a, and since both coils are being driven at the same frequency, the ratio between the voltage across the primary coil and that across the sense coil may be expressed as follows:

$$V_{primary}/V_{sense} = N_{primary}/N_{sense} \quad \text{Equation 5}$$

Thus, the ratio between $V_{primary}$ and $V_{sense}$ is determined by the ratio between the number of turns in the primary coil, $N_{primary}$ and the number of turns in the sense coil, $N_{sense}$.

As stated above, for a given recharge application, the antenna configuration that is optimally used to accomplish recharge may vary. As an example, one type of antenna assembly may be adapted for incorporation into a pillow for use in recharging a device located in a person's head while the person sleeps. Another type of antenna assembly may be configured to recharge an IMD buried in an angled fashion within a person's torso. Still another type of antenna assembly may be suited for recharging an IMD located in a person's chest cavity. In all of these examples, the number of coil turns, the coil size, and the coil shape of a primary coil 76 provided by the antenna assembly will be selected based on the recharge application and/or IMD for which it will be used.

According to one aspect, by including a sense coil in conjunction with a given primary coil and selecting a ratio between $N_{primary}$ and $N_{sense}$, the ratio between $V_{primary}$ and $V_{sense}$ may be maintained. This is true regardless of the antenna configuration, thus making different antennas configurations interchangeably connectable with the same recharging device 70.

Sense coil 104a may, but need not, be the same shape and size as the primary coil 76a with which it is associated. For instance, the sense coil 104a may be larger or smaller than the primary coil 76a. Preferably, sense coil 104a is smaller than primary coil 76a both to minimize the size of antenna, and to optimally sample magnetic flux in the primary coil 76a. When the two coils are of different areas, the relationship between $V_{primary}$ and $V_{sense}$ may also be controlled by selecting the shape and size of the sense coil, which determines the area of sense coil $A_{sense}$. The relationship in this scenario is as follows:

$$V_{primary}/V_{sense} = N_{primary} \times A_{primary}/V_{sense} \times A_{sense} \quad \text{Equation 6}$$

Thus, in this case, the relationship between $V_{primary}$ and $V_{sense}$ may be maintained by selecting both the number of turns and area in the sense coil based on the primary coil design needed for a given implant scenario.

As previously discussed, in one embodiment, the maximum voltage across the sense coil, $V_{max\_sense}$, is programmable by utilizing control circuit 88 to select voltage $V_{clamp}$ at the positive input of amplifier 114. The maximum sense voltage may be selected based on government regulations that dictate electrical and magnetic characteristics of devices for recharging IMDs. Such regulations may vary from jurisdiction to jurisdiction. A programmable embodiment allows such variations to be taken into account. It may further be desirable to vary $V_{clamp}$ based on the implant scenario, as will be discussed below.

In an alternative embodiment, $V_{clamp}$ may be a fixed value that is not variable, and $V_{max\_sense}$ may instead be selected by making the values of one or more of resistors R1, 116 and/or R2, 120 programmable according to Equation 3, above. In this embodiment, $V_{max\_sense}$ will generally be selected so that the maximum voltage across a primary coil, $V_{max\_primary}$, will be no greater than that for which coil interface 82 of recharging device 70 is rated.

The system of FIG. 4 further includes additional optional aspects, such as programmable switch 124 that is controllable by control circuit 88. Switch 124 may optionally be used to couple node 126 to the input of a rechargeable power source 128, which may be associated with one or more de-coupling capacitors (not shown) such as electrolytic capacitors or other batteries. The current generated by voltage limiting circuit 92 during the voltage clamping operation is then used to return energy to rechargeable power source 128, as by storing charge on such de-coupling capacitors. This recharging of the de-coupling capacitors may occur at the same time energy is being supplied by the rechargeable power source 128 to the recharging device 70.

Rechargeable power source 128 may be part of, or may serve as, power source 72 of FIG. 2. In some cases, rechargeable power source 128 may further replace power conversion circuit 74 of FIG. 2. Rechargeable power source 128 may be adapted to couple to a battery charger that plugs into a standard outlet for use in supplementing the charge received via the voltage clamping operation. In another embodiment, rechargeable power source 128 may be replaced by a non-rechargeable power source and switch 124 may be eliminated.

Restoring energy to the rechargeable power source 128 in the foregoing manner is possible when $V_{clamp}$ is selected such that $V_{max\_sense}$ is greater than the battery voltage $V_{batt}$ plus the voltage drop across the diode 118, $V_{diode}$. When $V_{clamp}$ is selected such that $V_{max\_sense}$ is less than battery voltage $V_{batt}$ plus the voltage drop across the diode 118, switch 124 should be programmed in the other position to allow current that is being sunk by the amplifier 114 according to arrow 122 to be dissipated by resistor 130 to maintain compliance.

The system of FIG. 4 may further include a frequency determining circuit 132 and a self-tuning oscillator, which is shown as a self-tuning oscillator 140. When these circuits are coupled to share a common ground (e.g., node 139 is coupled to a ground of self-tuning oscillator), the circuits are able to determine the resonant frequency of the system as follows. When primary coil 76a is being driven by an oscillating waveform such as a sine wave, diode 132a of frequency determining circuit 132 will conduct current during roughly half the waveform cycle while diode 132b is reversed biased, and diode 132b will conduct during the reminder of the waveform cycle while diode 132a is reversed biased. At the time when one diode is becoming reversed biased and the other diode is becoming forward biased, the voltage amplitude on feedback interface 133 is approximately zero volts. This signal is provided to a self-tuning oscillator 140 of modulation circuit 75, which may include a Colpitts oscillator, a Hartley oscillator, or some other self-tuning oscillator, for instance. Self-tuning oscillator 140 utilizes the signal provided on feedback interface 133 to drive coil selection circuit 80 (FIG. 2) at the resonant frequency of the tuned antenna configuration.

In an embodiment, self-tuning oscillator 140 determines the resonant frequency of the loaded system by varying the drive frequency at which coil interface 82 is driven. Modulation circuit 75 then measures the current driving the primary coil. When the drive current is determined to be at a maximum, the impedance of the energy transfer system is at a minimum. This frequency will be the resonant frequency at which the system is optimally driven. A detailed description of a self-tuning oscillator is provided in commonly-assigned patent application entitled "External Power Source for an Implantable Medical Device Having an Adjustable Carrier Frequency and System and Method Related Therefore", U.S. patent application Ser. No. 10/836,602 filed Apr. 30, 2004, which is incorporated herein by reference in its entirety.

If desired, self-tuning oscillator 140 may adjust the frequency at which recharge occurs not only initially during the commencement of energy transfer, e.g., charging, but also periodically during energy transfer. This may be useful if resonant frequency of the system changes somewhat because of a shifting in position or orientation of one or more primary coils 76 relative to secondary coil 56 of IMD 2. As an example, drive frequency can be constantly updated to seek resonant frequency perhaps every few minutes or every hour as desired. Periodically re-tuning for resonant frequency will reduce the amount of time recharging device 70 will need to be operated for a given amount of energy transfer, e.g., a given amount of battery charge. A reduced energy transfer, or charging, time can result in a decrease in the amount of heating of IMD 2 and surrounding tissue of patient 4.

In any of the above-mentioned ways, modulation circuit 75 is enabled to drive coils 76 at approximately the resonant frequency of the system, regardless of what that resonant frequency may be. This allows recharging device 70 to be removably coupled to any type of coil array containing one or more coils without regard to configuration (e.g., size, shape, area, number of turns, etc.) of the coils, and without regard to potential loading by the IMD, which will be affected by IMD coil shape and size, implant depth, coil orientation within a body, and so on. Preferably, in an array of multiple coils, all coils in the array include a same coil configuration, which will allow self-tuning oscillator 140 to more quickly and efficiently determine the resonant frequency of the system. If this is not the case, and an array of multiple coils includes coils of differing configurations and differing resonant frequencies, it is preferable that only a single coil be enabled to be driven by modulation circuit 75 at a given time. This will be discussed below in reference to FIG. 5B.

As may be appreciated, if sense coil 104a is not operating properly to limit voltage across primary coil 76a, the voltage across primary coil 76a will continue to increase until a steady-state condition occurs. This steady-state condition will exist when the energy being added to the system by modulation circuit 75 to drive primary coil 76a during each cycle is equal to the energy that is being dissipated each cycle because of the impedance of the loaded coil. This steady state may not be reached until the voltage across primary coil well exceeds the power rating of recharging device 70 and/or limits set by government regulations. Moreover, such voltage levels across primary coil 76a may expose the patient to unwanted magnetic field levels.

In view of the foregoing, it is desirable to detect when a fault in the sense coil interface is preventing sense coil 104a from limiting voltage across corresponding primary coil 76a. For instance, such a fault may involve an open or a short on one or more of lines 134 and 135 of the sense coil interface. If such a fault occurs, voltage across sense coil 104a will not be tracking the voltage signal across the primary coil, and circuit 132 will therefore not be providing a corresponding signal on feedback path 133 to self-tuning oscillator 140. In one embodiment, this signal on feedback path 133 is necessary for self-tuning oscillator 140 to enable modulation circuit 75 to drive primary coil 76a. Therefore, loss of this feedback signal will cause modulation circuit 75 to stop driving primary coil 76a, thereby disabling the recharge signal when a fault occurs on the sense coil interface, and preventing the voltage across primary coil 76a from reaching unwanted levels.

As described above, the feedback path 133 is provided to allow self-tuning oscillator 140 to drive the primary coil(s) 76 at the resonant frequency of the loaded system. This feedback may also be useful in determining a resonant frequency at which telemetry transmissions are to occur to an IMD. Feedback path 133 also provides a failsafe method to stop modulation circuit 75 from driving the primary coils 76 when a fault associated with the sense coil interface has prevented sense coil(s) from limiting voltage on the primary coil interface.

In some embodiments, recharging device 70 is not coupled to a dedicated telemetry antenna. Rather, telemetry module 86 of recharging device 70 communicates to IMD 2 via a selected one of primary coils 76. According to the current disclosure, a universal recharging device 70 that is intended for use with various IMD designs will not have a pre-selected frequency at which telemetry communication will be initiated. Rather, recharging device 70 will select the frequency of operation that is appropriate for accomplishing communication during each recharge session.

In one embodiment, selection of a frequency for performing telemetry communication is accomplished by modulation circuit 75, which drives the selected one of primary coils 76 with a pulse of energy. If the primary coil is positioned to inductively couple to a telemetry coil of IMD 2, this telemetry coil of the IMD and the circuit to which it is coupled will experience ringing as a result of the pulse of energy in the primary coil. After the pulse of energy in the primary coil 76 is discontinued, the selected primary coil 76 and/or the associated sense coil 104 may then be used to "listen" to the ringing. That is, a corresponding ringing will occur within the primary coil 76 and the associated sense coil 104 as a result of the inductive coupling between these coils and the telemetry coil of the IMD 2. The frequency of this ringing may be determined by recharging device 70, as by using frequency determining circuit 132 and self-tuning oscillator 140. This determined frequency may then be used to carry out telemetry uplink and downlink sessions between recharging device 70 and the IMD.

It may be noted that if IMD 2 has both a telemetry coil and a recharge coil with different resonant frequencies, care must be taken to ensure that the ringing being detected is occurring in the telemetry, and not the recharge, coil. In this embodiment, frequency isolation is necessary such that one range of possible resonant frequencies exists for telemetry transmission, and another range of frequencies exists for recharge. If the frequency that is detected as the result of ringing in an IMD circuit is outside of the expected range of frequencies used for telemetry transmission, the position of the antenna may be adjusted and the process repeated until a frequency in the expected telemetry range is detected.

The foregoing discusses an embodiment wherein $V_{max\_sense}$ is programmably selectable by selecting clamp voltage $V_{clamp}$ and/or a gain of amplifier 114 (as by selecting values for R1 and R2). In an alternative embodiment, voltage amplitude $V_{clamp}$ and the resistance values of R1 and R2 may be fixed such that $V_{max\_sense}$ is likewise fixed.

In yet another embodiment, rechargeable power source 128 and programmable switch 124 may be eliminated. In this case, energy is removed from the system via resistor 130 when amplifier 114 begins to sink current. In this case, recharging device 70 may be power by a non-rechargeable power source, if desired.

According to another aspect, feedback control may be provided to modulation circuit 75 to indicate when sense coil 104a begins to limit voltage across the interface. In particular, a compare circuit 137 may be provided to compare $V_{clamp}$ to $V_{sense}$ to determine when the following relationship exists between the two voltages:

$$V_{sense} = V_{clamp}(1 + R1/R2) + V_{diode} \quad \text{Equation 7}$$

This relationship will exist at the time sense coil 104a begins to draw energy out of the system by causing current to flow through amplifier 114 in the direction of arrow 122. When compare circuit 137 detects this condition, feedback signal 138 is provided to modulation circuit 75 to cause modulation circuit 75 to decrease the amount of energy modulation circuit 75 is adding to the system during recharge. For instance, modulation circuit 75 may decrease the voltage amplitude, current amplitude, and/or frequency at which primary coil 76a is being driven such that the energy being added to the system by modulation circuit 75 is decreased. In this manner, $V_{primary}$ and $V_{sense}$ may be decreased to an amplitude below that at which voltage limiting circuit 92 is draining energy from the system. This will reduce the energy that is being consumed by recharging device 70, which is particularly desirable in a system wherein recharging device 70 is being powered by a rechargeable power source 128, such as batteries.

Figure 5A:
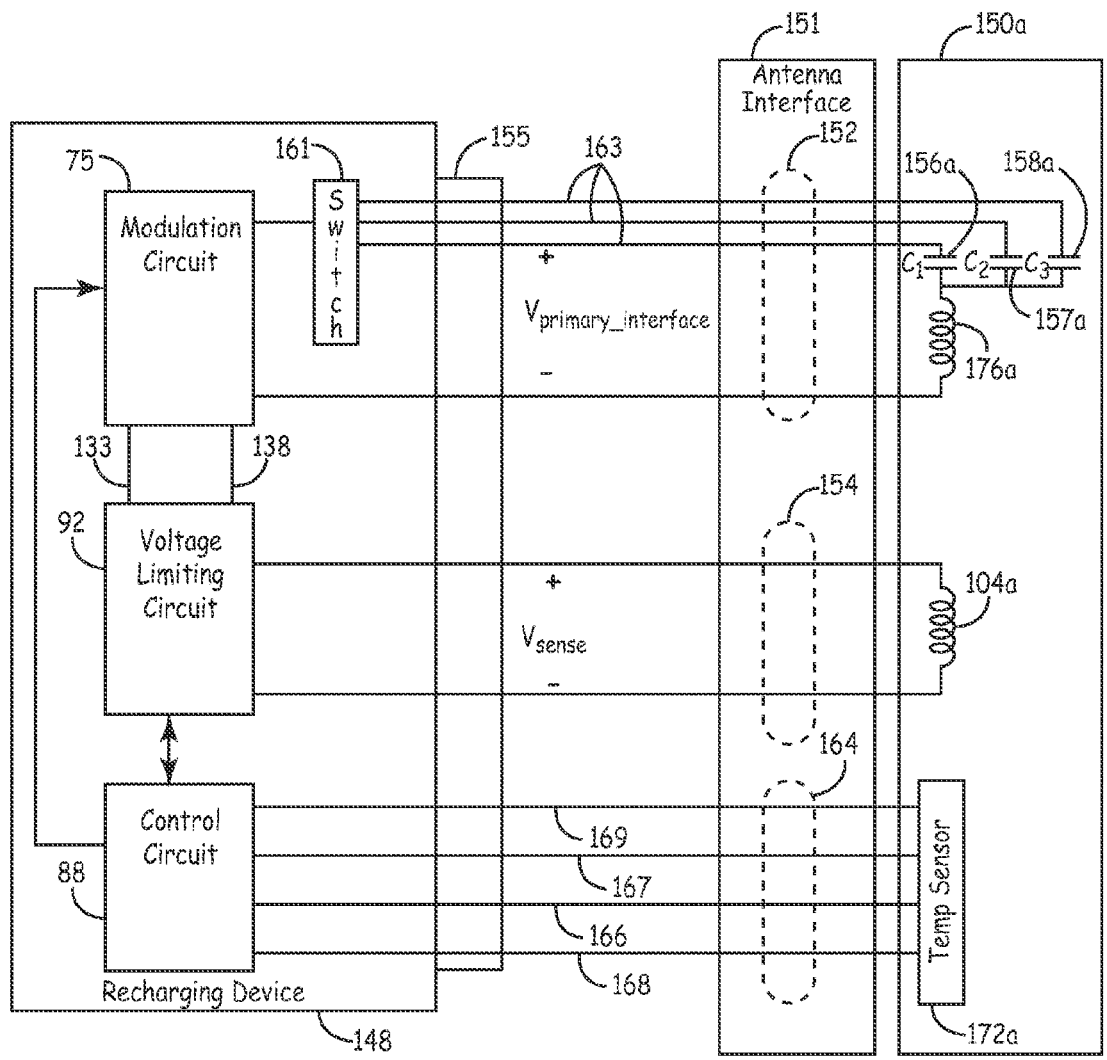
FIG. 5A is a schematic diagram of a recharging device coupled to a single antenna assembly according to the current disclosure.

FIG. 5A is a block diagram of the interface of recharging device according to the current disclosure. While FIG. 5A is simplified for ease of reference, it will be understood that recharging device 148 of FIG. 5A may include some, or all, of the sub-systems shown in regard to the recharging device 70 of FIG. 2 and/or the voltage limiting circuit 92 of FIG. 4. For instance, recharging device 148 may, but need not, include telemetry module 86, control circuit 88, coil selection circuit 80, and so on shown in FIG. 2 with respect to recharging device 70. Additional components may likewise be included in the embodiment of FIG. 5A, such as additional sensors.

FIG. 5A illustrates recharging device 148 being coupled to one antenna assembly 150a via an antenna interface 151. Recharging device 148 may be similar to recharging device 70 of FIG. 2. Antenna interface 151 includes a primary coil interface 152, a sense coil interface 154 (or "voltage limiting interface"), and an optional auxiliary interface 164 (all shown dashed).

Antenna assembly 150a includes primary coil 176a which may, for instance, correspond to primary coil 76a of FIGS. 2 and 4 in one embodiment. Primary coil 176a is coupled in series to capacitor 156a and is further coupled to recharging device 148 via primary coil interface 152 and connector 155.

Interface 152 is a low-impedance interface, as will be discussed further below in reference to FIG. 5B.

Capacitor 156a is optionally provided as a tuning capacitor having a capacitance of C1. Providing the tuning capacitor within antenna assembly 150a accomplished two key objectives. First, this allows tuning of the antenna to be made more coil-specific. The value of capacitor 156a, which may be chosen based on the design of coil 76a, will determine the resonant frequency at which coil 76a should be driven. Additionally, providing the capacitor within antenna assembly 150a limits the voltage across interface 152. This is because the potentially high voltage that typically develops across coil 176a will be about 180 degrees out of phase with the voltage across capacitor 156a, thereby limiting the voltage across interface 152. This is desirable for safety considerations.

As discussed above, capacitor 156a is shown to have a value $C_1$. As such, the optimal frequency $F_1$ at which coil 176a will be driven is as follows:

$$F_1 = \frac{1}{2\pi\sqrt{LC_1}} \quad \text{Equation 8}$$

wherein L is the inductance of coil 176a. Self-tuning oscillator 140 (FIG. 4) of modulation circuit 75 may be used to tune the system to drive interface 152 at this frequency.

In an alternative embodiment, antenna assembly 150a may include multiple additional tuning capacitors, such as tuning capacitors 157a and 158a shown to have respective capacitances of $C_2$ and $C_3$. Any number of such additional tuning capacitors may be included in the antenna design. Each such capacitor has one terminal coupled to coil 176a and another terminal coupled to a respective one of conductors 163 that returns to connector 155.

In one embodiment, a switching element 161 (shown as "switch 161") is included within recharging device 148. Switching element 161 may be a low impedance switch or any other circuit capable of selectably coupling modulation circuit 75 to one or more circuit nodes (e.g., a high-power multiplexing circuit). This element optimally has an impedance substantially lower than any of the capacitor/coil pairs, and may be used to select which of the multiple in-series capacitor/coil pairs modulation circuit 75 will drive at a given time. In one embodiment, switching element is programmably controllable, as by control circuit 88 or some other means of control.

Switching element 161 allows the resonant frequency $F_X$ of interface 152 to be selected as follows:

$$F_x = \frac{1}{2\pi\sqrt{LC_x}} \quad \text{Equation 9}$$

where $C_X$ is the capacitance of the selected capacitor/coil pair (in this example, C1, C2, or C3).

In yet another embodiment wherein switching element 161 may be configured so that modulation circuit 75 drives multiple capacitors 156a, 157a, and 158a along with coil 176a, yet another resonant frequency may be obtained that is based on multiple ones of the capacitances $C_1$ through $C_N$ (e.g., C1 through $C_3$) as follows:

$$F_y = \frac{1}{2\pi\sqrt{L(\sum C_N)}} \qquad \text{Equation 10}$$

wherein the sum of $C_N$ includes a sum of all capacitances of all capacitors that are being driven. For instance, if all three interfaces coupled to all three of the capacitors are enabled by switching element 161 to be driven in parallel, the resonant frequency is as follows:

$$F_y = \frac{1}{2\pi\sqrt{L(C_1 + C_2 + C_3)}} \qquad \text{Equation 11}$$

The resonant frequency may be based on the capacitances of fewer than all of the capacitors if fewer than all capacitors are programmably enabled by switching element 161 to be driven in parallel.

In the foregoing manner, the resonant frequency of antenna assembly 150a may be selected using switching element 161 in one embodiment. It may be desirable to utilize this capability to configure antenna assembly 150a for one resonance frequency when a recharge operation is being conducted, and a different resonant frequency when telemetry communication is occurring between recharging device 146 and IMD 2.

In one embodiment, antenna interface 151 is physically embodied in a cable that couples to antenna assembly 150a and that further removably couples to recharging device 148. In one embodiment, the various capacitors 156-158 shown in FIG. 5A to be carried by antenna assembly 150a may instead be included within, or carried by, this cable. For instance, a module containing circuit components such as capacitors 156-158 may be integrated with a cable that carries antenna interface 151. Such a circuit module may optionally incorporate other circuit elements, such as switch 161, which may be controlled by one or more signal lines transmitted from recharging device 148. Thus, the manner in which the various elements are partitioned in FIG. 5A is illustrative only, and many alternative embodiments are possible.

Antenna assembly 150a may further include sense coil 104a which is coupled to recharging device 148 via sense coil interface 154 and connector 155. Sense coil 104a is adapted to limit the voltage across primary coil 176a to $V_{max\_primary}$ in a manner described above.

During use, primary coil 176a is inductively coupled to secondary coil 56 of IMD 2. Primary coil 176a is further inductively coupled to sense coil 104a such that a voltage is induced across this sense coil. The voltage across this sense coil will be limited to $V_{max\_sense}$ in the manner previously described such that the voltage drop across the loaded primary coil will be limited to $V_{max\_primary}$.

The voltage across primary coil interface 152, $V_{primary\_interface}$, reflects the voltage across the primary coil/capacitor in-series pair. This interface voltage will be less than the maximum voltage $V_{max\_primary}$ across primary coil 76a because the voltage across the capacitor 156a is approximately 180 degrees out of phase with the voltage across primary coil 76a.

FIG. 5A further illustrates control circuit 88, which may be a microprocessor as discussed above, coupled via connector 155 to an auxiliary interface 164 (shown dashed). In this illustration, the interface may be a Serial Peripheral Interface (SPI) or an Inter-Integrated Circuit (I2C). Such an interface may include two data lines 166, 167, and a ground line 168. The interface may further include a power line 169. The two data lines, as well as the power and ground connections may each be provided to a temperature sensor 172a. Such a temperature sensor may include thermistors, thermocouple devices, or any other type of temperature sensing devices, and a circuit to digitize the output for transmission via data lines 166, 167 to recharging device 148.

The temperature indication provided via data lines 166, 167 may be forwarded to control circuit 88, which may perform some type of processing of this temperature indication, and/or may then forward this indication to modulation circuit 75. In one embodiment, control circuit 88 may be replaced with a dedicated temperature detection circuit such as temperature detection circuit 94 (FIG. 2). In either case, the indication of temperature may be used to control the way modulation circuit 75 drives primary coil interface 152. For instance, if the temperature of antenna assembly 150a is determined to be too high, modulation circuit 75 may reduce the amplitude or frequency at which the primary coil interface 152 is driven to reduce the energy transferred to primary coil 176a. This reduces the temperature of antenna assembly 150a. In this manner, temperature of antenna assembly 150a may be controlled according to government regulations, other safety standards, or patient preferences.

In a simplified embodiment, auxiliary interface 164 may be omitted entirely if temperature sensing at the antennas is not considered important to the particular application that is in use.

Any type of mechanical connector may be employed to implement connector 155 of recharging device 148. For instance, the connector may be a co-axial connector, an RF connector, a Type N connector, a SnapN connector, or any of the other myriad of connector types available. The connector may take a cylindrical form such as shown in some of the examples, or may take a different form, so long as the connector at least supports the primary coil interface 152 and sense coil interface 154 shown in FIG. 5A. The connector may optionally support temperature sense interface 164.

Figure 5B:
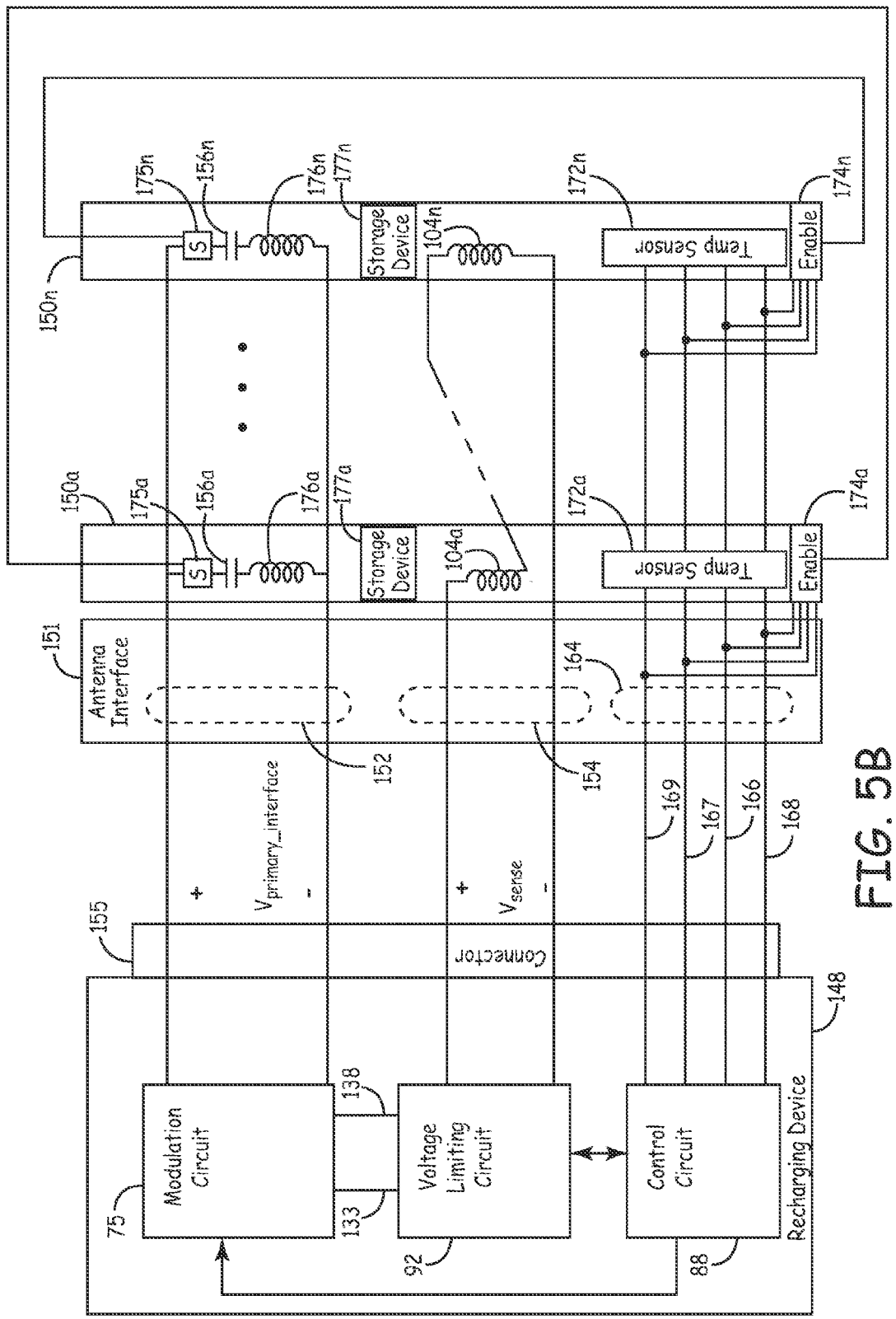
FIG. 5B is a schematic diagram of a recharging device coupled to multiple antenna assemblies according to the disclosure.

FIG. 5B illustrates recharging device 148 being coupled to multiple antennas 150a-150n (hereinafter, "antennas 150") via an antenna interface 151. In this figure, elements similar to those of FIG. 5A are labeled with like numeric designators. Each antenna includes a respective one of primary coils 176a-176n, each of which may, in one embodiment, correspond to primary coils 76a-76n of FIGS. 2 and 4. Each of the primary coils 176a-176n may be coupled in series to a respective capacitor 156a-156n. If desired, each primary coil may further be coupled to additional capacitors in the manner shown in FIG. 5A such that the resonant frequency of each coil is selectable. Each in-series coil/capacitor pair of a particular antenna assembly 150 may be coupled to all such other in-series coil/capacitor pairs of other antennas 150 in parallel via primary coil interface 152.

Primary coil interface 152 and connector 155 represent an impedance common to all coils. To prevent the load on one coil from reducing the drive voltage available to another coil, the impedance of the primary coil interface 152 and connector 155 must be kept low.

In a manner similar to that shown in FIG. 5A, each antenna assembly 150 further includes a respective one of sense coils 104a-104n. In the illustrated embodiment, sense coils 104 are coupled to one another in series. The sense coils 104 are coupled to recharging device 148 via sense coil interface 154 (shown dashed) and connector 155. Each sense coil 104 is adapted to limit the voltage across a corresponding primary coil 176 to $V_{max\_primary}$ in a manner described above.

In the multi-antenna embodiment of FIG. 5B, all of the antenna assemblies may be of the same configuration. That is, each such antenna assembly 150 may have a primary coil 176 that has the same number of turns, the same area, and is nominally of the same inductance as the other primary coils 176. Similarly, each antenna assembly 150 may have a capacitor 156 that is nominally of the same capacitance as the other capacitors 156. The sense coils 104 may likewise all be of a same configuration. Alternatively, some of the antenna assemblies 150 may be of different configurations.

In an embodiment wherein multiple primary coils are available as shown in FIG. 5B, it may be desirable to enable only one of the primary coils for use at a given time, with all other primary coils being disabled. This may be particularly beneficial if the antenna assemblies have different configurations, and thus do not all have the same resonant frequency. In this case, disabled primary coils may be disconnected from modulation circuit 75 via high-power switches. To accomplish this, enable circuits 174a-174n ("enable circuits 174") may be provided that are coupled to, and powered by, the interconnections of auxiliary interface 164. As discussed above, interface 164 may be implemented using an I2C or a SPI interface that includes multiple data lines 166, 167, a ground line 168, and a power line 169. Enable circuits 174 are addressable, as by control circuit 88, which provides an address and commands via data lines 166 and 167. When an enable circuit 174 detects that it is being addressed, it may open or close a respective one of high-power switches 175a-175n ("switches 175). The opening and closing of a switch may be performed based on a command received via auxiliary interface 164 by the enable circuit 174. In this manner, control circuit 88 will control which of antennas 150 will be enabled for use at a given time.

Assuming that only a single primary coil is enabled for use at a given time, modulation circuit 75 will drive the enabled primary coil such that a voltage will appear across this coil, and this coil will be inductively coupled to a secondary coil of the IMD. None of the other primary coils will be driven, or will exhibit any substantial voltage drop across the coils. The enabled one of the primary coils 176 will be inductively coupled to the corresponding sense coil 104 in the same antenna assembly such that a voltage is induced across this sense coil. The voltage drops across the sense coils that reside in the unused antenna assemblies (i.e., the sense coils associated with the disabled primary coils) will be minimal. In this manner, substantially the entire voltage drop $V_{sense}$ across sense coil interface 154 will appear across the sense coil that is associated with the enabled primary coil 176. The voltage drop across this sense coil will be limited substantially to $V_{max\_sense}$ in the manner previously described such that the voltage drop across the loaded primary coil will be limited to $V_{max\_primary}$. A lower voltage will appear across primary coil interface 152, $V_{primary\_interface}$, because the voltage across the in-series capacitor 156 is approximately 180 degrees out of phase with the voltage across the corresponding loaded primary coil 176.

In an embodiment wherein more than one, or all, of the multiple primary coils 176 and in-series capacitors 156 of antenna assemblies 150 are of a same configuration such that multiple primary coils have substantially the same resonant frequency, it may be desirable to have more than one antenna assembly 150 enabled at the same time to conduct a recharge session. In this case, control circuit 88 may directly enable circuits 174 to select multiple ones of the primary coils 176. Modulation circuit 75 may drive the system at a resonant frequency that is common to all such primary coils. In this case, the voltage drop $V_{sense}$ across sense coil interface 154 will appear across multiple sense coils that are associated with the loaded primary coils, rather than just across a single sense coil. As such, the maximum voltage across any one of the sense coils 104 will be less than $V_{max\_sense}$. Correspondingly, the maximum voltage across the loaded primary coils 176 will be limited to something less than $V_{max\_primary}$. In such a configuration wherein only a portion of $V_{max\_sense}$ will appear across each of multiple selected coils, it may be desirable to increase the value for $V_{max\_sense}$ so that the voltage across each individual coil may be increased to a desired amplitude.

Enabling multiple ones of the primary coils at once is generally not desirable when all antenna assemblies 150 do not share a same resonant frequency either because all primary coils 176 are not of a same inductance and/or because all capacitors 156 are not of a same capacitance. In this case, self-tuning oscillator 140 will not be able to determine a resonant frequency common to all antenna assemblies such that some of the primary coils must be disabled prior to initiating a recharge session.

Each antenna assembly may contain identification data that describes the antenna assembly. For instance, this data may identify a recharge scenario for which the antenna assembly is suited. Such identification may be stored in storage devices 177a-177n that may comprise Read-Only Memories (ROMs), flash memory devices, RFID tags, or in other storage device. Enable circuits 174 may incorporate these storage devices in one embodiment. The stored data may indicate a type of IMD, a location of implant, an implant depth, and/or any other information that identifies the type of antenna and its intended use. This information may be read by control circuit 88 via auxiliary interface 164, or may be read by a transmitter adapted to read RFID tags.

Using the above-described mechanism, a user of recharging device 148 may provide information concerning a recharge session that is to be initiated, as may be accomplished using a patient or a clinician programmer, for instance. This provided information may indicate a type of IMD that is involved, an implant location, implant depth, implant orientation, and so on. Control circuit 88 may read information from each antenna assembly to which it is physically connected. Based on this information, control circuit 88 may enable only the one or more antenna assemblies 150 that are applicable to the type of recharge scenario that will be involved in the recharge session. In addition, control circuit 88 may re-select the clamping voltage $V_{clamp}$ for certain applications. For instance, it may be desirable to increase this voltage somewhat for deep or angled implant scenarios, thereby allowing a larger magnetic field to be generated at the primary coil. In any event, $V_{clamp}$ will not be selected to allow a primary coil voltage above that for which recharging device 148 is rated.

If recharging device 148 is always used in a same type of scenario (e.g., is always used with the same antenna assembly), a "Save Configuration" command may be used to save, and thereafter use, a set configuration that determines the enabled antenna assembly 150 and the value of $V_{clamp}$ so that the configuration need not be re-determined prior to each recharge session. In this case, a "Reconfigure" command must be executed prior to performing a recharge session with a different antenna assembly and/or with different configuration settings (e.g., different $V_{clamp}$ setting).

As described herein, multiple antenna assemblies adapted for use in various recharge scenarios and applications may remain physically coupled to recharging device 148 in parallel, which may be advantageous in a clinical setting. For instance, an antenna assembly design that is adapted to recharge an IMD that is typically associated with a deep or angled implant scenario may remain physically coupled in parallel to recharging device 148 along with an antenna assembly having a coil configuration of a different size, shape and/or number of coil turns, and that is adapted for recharging a more shallowly-implanted IMD. This may eliminate the need for a clinician to be required to disconnect/re-connect and locate various antenna assemblies for different patients. Assuming an appropriate cable connection system is available to achieve the in-parallel configuration of antenna assemblies 150 as shown in FIG. 5B, some or all available antenna assemblies may remain plugged into recharging device 148 and are ready to use. The clinician need only identify the antenna that is applicable for a given implant scenario from among the available antenna assemblies.

Of course, as previously described in reference to FIG. 5A, recharging device 148 and antenna assemblies 150 may be designed such that recharging device 148 is physically coupled to only a single one of antenna assemblies 150 at once. In this embodiment, a clinician and/or patient will determine which of the antenna assemblies 150 is needed to conduct recharge for a particular implant scenario and connect that antenna individually to recharging device 148. This embodiment is preferable if recharging device 148 is used in scenarios wherein the patient is ambulatory, since the patient will not be required to tote multiple unused antenna assemblies along with the recharging device.

FIG. 5B further illustrates that each of the antenna assemblies 150a-150n includes a respective one of temperature sensors 172a-172n coupled to auxiliary interface 164. These sensors may be coupled in parallel or in series. Each antenna assembly may transmit temperature information to control circuit 88. In general, transmission of temperature information will only be performed for those antenna assemblies 150 having enabled primary coils 176.

In an embodiment wherein multiple primary coils 176 are utilized, the multiple primary coils 176 and corresponding sense coils 104 may be mechanically coupled to one another in a variety of ways, as shown in reference to FIGS. 6A-6C.

FIG. 6A is a side view of an array having antenna assemblies 180a-180n ("antenna assemblies 180"). Each antenna assembly 180 contains a respective primary coil 176 and sense coil 104 (not shown in FIG. 6A) electrically connected in the manner similar to that discussed above. In this example, each of antenna assemblies 180 has a curved cross-sectional shape, although one or more of the antenna assemblies may be substantially flat, or have some other cross-sectional shape. The primary coil and sense coil that are housed within this antenna assembly (not shown) may likewise have a shaped cross-section corresponding to the antenna assembly cross-section, if desired.

Each of antenna assemblies 180 may have a same configuration, or some of the antenna assemblies may be of a different configuration as described above in reference to FIG. 5B. For instance, the primary coils of some of the antenna assemblies 180 may have a different size, number of coil turns, different shapes, and so on such that one coil has a different inductance than others of the primary coils of different ones of antenna assemblies 180. In each case, a sense coil configuration is selected to match the corresponding primary coil configuration, and to ensure that the maximum voltage across each corresponding primary coil will be limited to no greater than the maximum voltage for which the recharging device (e.g., connector 155 of recharging device 148 and coil interface 82 of recharging device 70) is designed, and that further conforms to regulatory electrical and magnetic field strength requirements. In one embodiment each antenna assembly 180 (including the corresponding coils) may be made of flexible material that conforms to the body.

Each antenna assembly 180a-180n is coupled to connector 184 through a respective cable 182a-182n. Each such cable 182 carries the various electrical connections needed to support antenna interface 151 for the respective antenna assembly. Connector 184 may be designed to electrically and mechanically couple with connector 155 of recharging device 148. When so coupled, the primary coils 176 and respective sense coils 104 housed by antenna assemblies 180 are electrically coupled in the manner shown in FIG. 5B. That is, the primary coils 176 are connected in parallel via primary coil interface 152, sense coils 104 are coupled in series to sense coil interface 154, and one or more antenna assemblies may optionally be coupled in series or in parallel to a respective one of auxiliary interfaces 164. Switches 175 and enable circuits 174 may be provided by one or more of antenna assemblies 180.

As discussed above, one or more of cables 182a-182n may include an enlarged portion 183 that houses a circuit module. The circuit module may carry various circuit components, if desired. For instance, enlarged portion 183 of cable 182a may house a circuit module carrying capacitors (e.g., 156a-158a of FIG. 5A), a high power switch such as switch 175a (FIG. 5B), temperature sensor 172a, enable circuit 174a, and/or one or more other circuit components. Thus, some of the circuit components may be carried or housed by a cable assembly coupled to the antenna assembly rather than by the antenna assembly itself.

FIG. 6B is a top view of one example of the antenna array of FIG. 6A. Each antenna assembly 180 in the array is shaped as a toroid, although the antenna assemblies may be formed in any other shape (e.g., square, triangle, oblong, rectangle, irregular shape, circular, etc.).

FIG. 6C is a top view of an antenna array having antenna assemblies 190a-190n ("antenna assemblies 190") that are coupled in a two-dimensional array. In this example, each of the antenna assemblies is square, although one or more of antenna assemblies 190 may have any other shape that is more optimally suited to a given recharge application. All of the antenna assemblies 190 are coupled via cable 192 to connector 194, which is adapted to electrically and mechanically couple to connector 155 of recharging device 148. The antenna array of FIG. 6C may be flexible such that is conforms to three-dimensional objects and contours.

As was the case in regard to FIG. 6A, each of antenna assemblies 190 houses a primary coil 176 and a respective sense coil 104 (not shown in FIG. 6C). One or more antenna assemblies may include a temperature sensor 172, an enable circuit 174, a switch 175, and one or more tuning capacitors (e.g., capacitors 156, 157, and 158 of FIG. 5A). When connector 194 is coupled to connector 155 of recharging device 148, the various primary and sense coils of antenna assemblies 190 are electrically coupled in the manner shown in FIG. 5B.

Figure 6D:
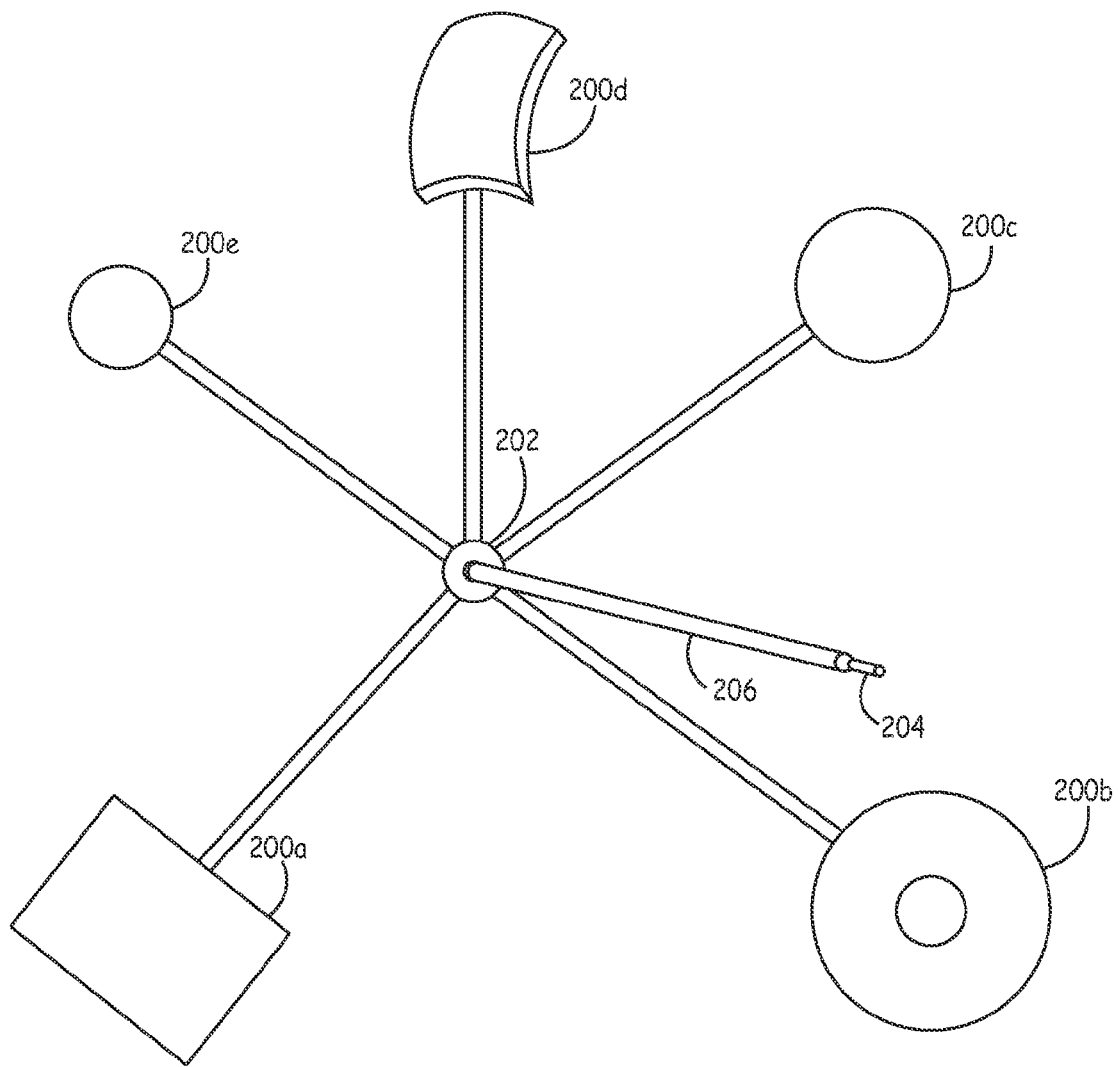
FIG. 6D is a top view of a multi-antenna array having various antenna configurations.

FIG. 6D is another example of various antenna assemblies configured in a "star" shape. The various antenna assemblies 200a-200e have different sizes and shapes in this example. The primary and sense coils housed by these antenna assemblies may likewise have varying sizes and shapes. Each such antenna assembly is coupled to a central hub 202 that is further coupled to a connector 204 via central cable 206. When connector 204 is coupled to connector 155 of recharging device 148, any one or more of the antenna assemblies 200 may be enabled for use at once during a recharge session. In this embodiment, one or more of an enable circuit and/or storage device to store identification information may be maintained within hub 202, if desired. As discussed above, the antenna assemblies that are selectively enabled will depend on the IMD and/or implant scenario that is associated with the recharge session.

The current disclosure provides a mechanism wherein a single universal design for a recharging device may be interconnected to many different antenna assembly designs. Each such antenna assembly includes at least one primary coil and a corresponding sense coil. The primary coil may be of various shapes, sizes, number of coil turns, and so on. The associated sense coil is configured to select an appropriate ratio between $V_{sense}$ across the sense coil and $V_{primary}$ across the corresponding primary coil. Further, the sense coil will limit the maximum voltage across the primary coil, $V_{max\_primary}$ based on selectable and/or hard-wired parameters of the recharging device (e.g., $V_{clamp}$ and amplifier gain). Moreover, a single cable may couple multiple antenna assemblies at once to recharging device. These antenna assemblies may have the same, or different, primary and/or sense coil designs. Self-tuning oscillator 140 may be provided to select a frequency at which to drive the system based on the antenna assembly configuration that is in use at a given time.

Tuning may further be enhanced by selectively enabling one or more of multiple available tuning capacitors such that the resonant frequency is selectable for a given antenna assembly. For instance, a first frequency may be selected for use during recharge and a different frequency may be selected for use during telemetry communication. In one embodiment, this tuning capability may also be used to allow the unused antenna assemblies to remain connected to recharging device without having any substantial affect on the recharging session, since the unused antenna assemblies that are not driven at their resonant frequency will add little to the loading of the system.

Various alternative embodiments exist within the scope of the disclosure. For instance, one or more of the circuits included in recharging device 70 or 148 may alternatively or additionally be included within one or more of antenna assemblies 78 and/or antenna assemblies 150. As an example, a control circuit (e.g., control circuit 88), which may be a microprocessor, state machine, an ASIC, or any other type of logic component(s), may be located within one or more of antenna assemblies 150 for receiving various commands via data lines 166 and 167. Such commands may control operations of the respective antenna assembly 150 (e.g., control of temperature sensing and/or reporting.). Thus, any number of additional circuits may be included within a given antenna assembly, and those shown in the various Figures are not to be considered limiting.

Figure 7:
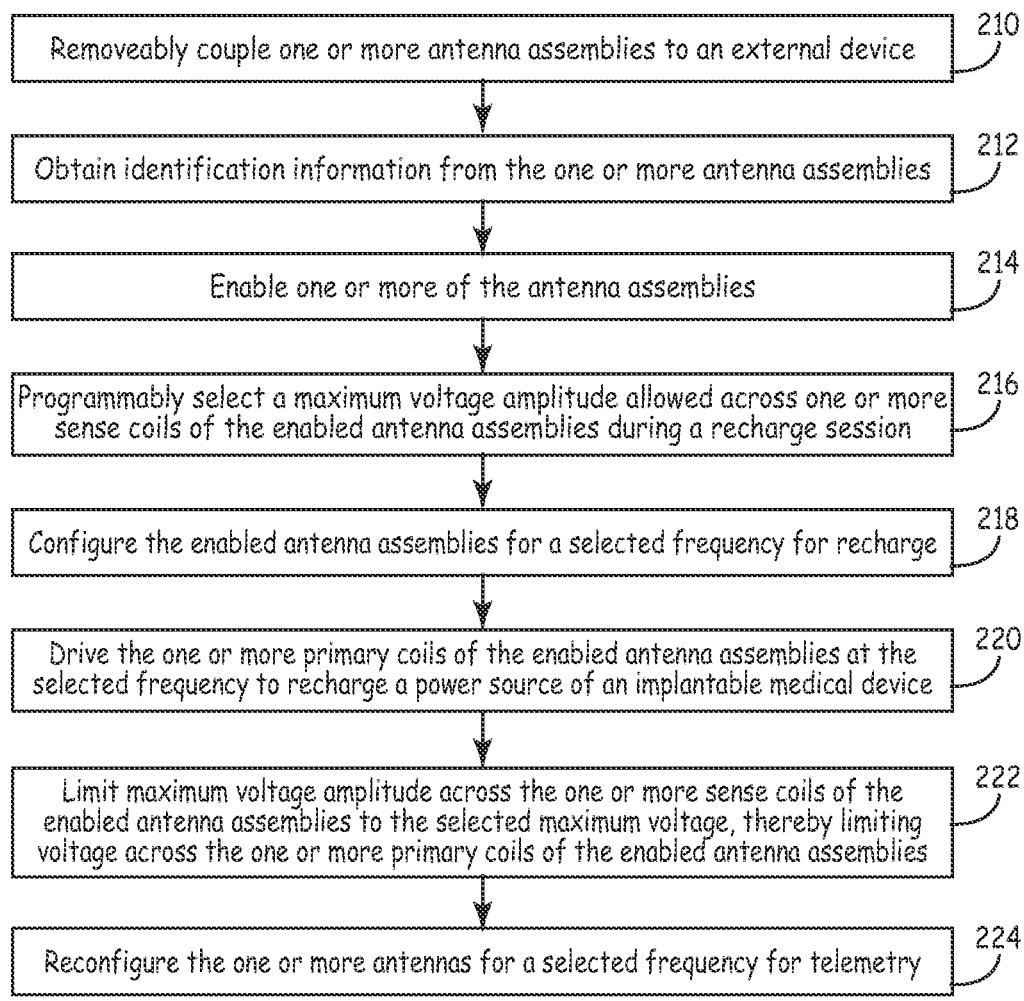
FIG. 7 is a flow diagram of a method according to the current disclosure.

FIG. 7 is a flow diagram of a method according to the current disclosure. One or more antenna assemblies are removeably coupled to an external device (210). The external device may be a recharging device, and may include programming capabilities. The antenna assemblies may be of any one or more multiple configurations. As discussed above, each antenna assembly includes a primary coil that is adapted for use in association with a particular type of implant scenario. The implant scenario may involve a particular type of IMD, a depth of implant, an orientation of implant, a location of implant within a body, a distance between the IMD and the primary coil, a size, shape and orientation of a secondary coil within the IMD, and so on. Each primary coil may be adapted for a particular use by varying the coil turns, coil size, and/or coil shape, for instance.

Each antenna assembly is further provided with a sense coil for use with the primary coil of the antenna assembly. The configuration of the sense coil is selected to maintain a given ratio between voltage across the sense coil and voltage across the primary coil when the antenna assembly is used during a recharge session. The configuration of the sense coil is varied by selecting the number of coil turns, coil shape, and coil size, for instance.

In one embodiment, identification may be read from the one or more antenna assemblies, as by using an RFID reader to read information from a passive or active RFID tag or by reading information from a storage device carried by the antenna assemblies (212). This identification information may identify a type of implant scenario for which the one or more antennas are adapted (e.g., type of IMD, implant depth, implant location, etc.) Based on this identification information or some other information, one or more of the antenna assemblies may be enabled for use (214). In a configuration wherein only a single antenna is coupled to the recharging device at a given time, this enabling step may be unnecessary, as may be the step of obtaining information describing the antenna assembly.

Next, a maximum voltage amplitude that may be allowed across one or more sense coils of the enabled antenna assemblies during a recharge session may be programmably selected (216). This may be accomplished, for instance, by selecting $V_{clamp}$ and/or by selecting a gain of an amplifier that is associated with the sensing coil(s). This maximum voltage amplitude may be selected based on the antenna assembly information obtained in step 212, if desired. In another embodiment, this step may be omitted if the maximum voltage amplitude is to remain the same regardless of the connected antenna assembly.

The system may further determine a frequency to be used during the recharge session (218). This may be accomplished, in part, by selectively enabling one or more tuning capacitors for use during a recharge session. The capacitors may be provided by one or more of the antenna assemblies, as shown in FIG. 5B. Alternatively or additionally, one or more tuning capacitors may reside within recharging device 148 itself. Frequency tuning may be performed by a self-tuning oscillator, as discussed above. If desired, information concerning resonant frequency for a given antenna assembly may be obtained from identification information garnered in step 212.

During recharging of a power source of an IMD, one or more primary coils of the enabled antenna assemblies may be driven at the selected frequency, which may be the resonant frequency of the system (220). While this is occurring the voltage amplitude across one or more sense coils of the one or more enabled antenna assemblies is limited to the selected maximum voltage (222). This limits maximum voltage amplitude across one or more primary coils of the one or more enabled antenna assemblies based on the selected maximum voltage. The voltage across the one or more primary coils of the enabled antenna assemblies will be no greater than the voltage for which the recharging device is rated, and optimally will meet government regulations concerning electrical and magnetic field strength specifications for recharging medical devices.

Optionally, the one or more antennas may be reconfigured for use with a different frequency (224). This may occur after recharge has occurred for some period of time, for example, and may be in preparation to initiate a communication session with the IMD via the one or more antennas. The communication session may be useful to determine whether effective recharge coupling has been established between the one or more enabled antenna assemblies and the IMD, for instance. This information may then be used to continue the interrupted recharge session, if desired.

It will be understood that the steps of FIG. 7 are largely exemplary. The steps may, in many cases, be re-ordered. Some of the steps may be eliminated entirely in various embodiments. For example, it may be desirable in some scenarios to utilize the voltage limiting capabilities described herein with an external device that only includes communication capabilities, and is not used for recharge. For instance, the external device of the method of FIG. 7 may be a clinician or patient programmer that is not used for recharge. In this type of scenario, the steps that are exclusively related to recharge (e.g., step 220) may be eliminated.

The various embodiments described herein may be practiced with any type of recharge and/or programming system, and recharging devices 70 and 148 of FIGS. 2, 5A, and 5B are understood to be merely exemplary. Moreover, any type of antenna configuration (antenna size, shape, material makeup, and so on) may be adapted for use with the current disclosure. Thus, the embodiments described herein, and the applications described for use of the embodiments, are to be considered exemplary only and not limiting, and the present invention is limited only by the claims that follow.

What is claimed is:

1. A system, comprising:
   a device adapted to charge a rechargeable power source of an Implantable Medical Device (IMD); and
   an antenna assembly physically removably coupled to the device, the antenna assembly having a primary coil and a corresponding sense coil, the sense coil having a configuration that is selected based on the configuration of the primary coil, the sense coil adapted to prevent voltage across the primary coil from exceeding a maximum voltage amplitude;
   wherein the primary coil is any selected one of multiple coil configurations, and wherein the device is adapted to drive any of the multiple coil configurations.

2. The system of claim 1, wherein the antenna assembly comprises a temperature sensor adapted to provide the device with an indication of temperature of the antenna assembly.

3. The system of claim 2, wherein the device comprises a modulation circuit adapted to modify a frequency at which the antenna assembly is driven based on the indication of temperature of the antenna assembly.

4. The system of claim 1, wherein the device comprises a voltage limiting circuit adapted to select the maximum voltage amplitude corresponding to a selected magnetic field limit.

5. The system of claim 4, wherein the maximum voltage amplitude is selected programmably.

6. The system of claim 1, wherein the device comprises a voltage limiting circuit that is adapted to recharge a rechargeable power source when the sense coil is preventing voltage across the primary coil from exceeding the maximum voltage amplitude.

7. The system of claim 1, further comprising multiple antenna assemblies adapted to be removably coupled to the device, each antenna assembly having a primary coil and a corresponding sense coil, each sense coil having a configuration that is selected based on the configuration of the corresponding primary coil, each sense coil adapted to prevent a voltage amplitude across the corresponding primary coil from exceeding the maximum voltage amplitude.

8. The system of claim 7, wherein the multiple antenna assemblies are adapted to be removably coupled to the device at once, and wherein each of the multiple antenna assemblies comprises an enable circuit adapted to selectively disable a corresponding primary coil, and wherein the device is adapted to drive only enabled ones of the primary coils when charging the rechargeable power source.

9. The system of claim 7, wherein at least one of the primary coils has a configuration that is different from that of another one of the primary coils.

10. The system of claim 7, wherein the primary coils are adapted to be coupled in parallel with one another.

11. The system of claim 7, wherein the sense coils are adapted to be coupled in series with one another to limit voltage across all of the primary coils from exceeding the maximum voltage amplitude.

12. The system of claim 1, further comprising a self-tuning oscillator adapted to determine the resonant frequency of the primary coil when the primary coil is recharging the power source of the IMD, and to drive the primary coil at the resonant frequency.

13. The system of claim 12, wherein the self-tuning oscillator is adapted to disable charging of the rechargeable power source when a fault occurs on an interface to the sense coil.

14. The system of claim 1, wherein the device comprises a frequency determining circuit adapted to determine a frequency at which the primary coil will initiate a communication session with the IMD.

15. The system of claim 1, wherein the antenna assembly comprises one or more tuning capacitors adapted to select a frequency at which the primary coil is to be driven.

16. The system of claim 15, wherein the device comprises a switching element adapted to select one or more of the tuning capacitors.

17. The system of claim 15, further comprising a control circuit adapted to select a first frequency at which the primary coil is to be driven during communication and to select a second frequency at which the primary coil is to be driven to charge the rechargeable power source of the IMD.

18. The system of claim 1, wherein the IMD is adapted to be implantable within a patient, the device is adapted to be external to the patient, and wherein the device is configured to transcutaneously charge the rechargeable power source of the IMD.

19. The system of claim 1, wherein the device includes a connector, and wherein the antenna is adapted to be removably coupleable to the connector of the device.

20. The system of claim 1, wherein the primary coil is any selectable one of multiple coil configurations, each of the multiple coil configurations varying from another of the coil configurations by at least one of coil size, coil shape, coil area, and number of coil turns.

21. For use with a recharge system that is adapted to recharge a rechargeable power supply of an implantable medical device (IMD), a system, comprising:
   a primary coil interface adapted to be physically removably coupled to a primary coil that is any of multiple coil configurations;
   a sense coil interface adapted to be physically removably coupled to a sense coil and to regulate voltage amplitude across the sense coil while the primary coil interface is being used to recharge the rechargeable power supply, thereby limiting voltage amplitude across the primary coil interface to a maximum voltage amplitude;
   a primary coil adapted to be coupled to the primary coil interface, the primary coil having a selected one of the multiple coil configurations; and
   a sense coil having a coil configuration that is selected based on the selected one of the multiple coil configurations.

22. The system of claim 21, further comprising an auxiliary interface adapted to transmit data.

23. The system of claim 22, further comprising a temperature sensor coupled to the auxiliary interface and adapted to provide an indication of a temperature of the primary coil.

24. The system of claim 21, wherein the sense coil interface electrically couples to a voltage limiting interface adapted to limit a maximum voltage amplitude across the sense coil.

25. The system of claim 21, wherein the primary coil interface is adapted to transmit a signal determining a frequency at which the IMD will communicate.

26. The system of claim 21, further comprising a device adapted to charge a rechargeable power source, and wherein at least one of the primary coil interface and the sense coil interface is adapted to be removably coupleable to a connector of the device.

27. The system of claim 21, further comprising a device adapted to couple to the primary coil interface, wherein the device is adapted to drive any of the multiple coil configurations.

28. The system of claim 27, wherein the multiple coil configurations vary from one another by at least one of coil size, coil shape, coil area, and number of coil turns.

29. An antenna assembly for use in recharging an Implantable Medical Device (IMD) having a secondary coil, the antenna assembly comprising:
a primary coil having a coil configuration selected from multiple possible coil configurations;
a sense coil having a coil configuration that is selected based on the selected coil configuration of the primary coil; and
a sense coil interface physically removably coupled to the sense coil, the sense coil interface adapted to limit strength of a magnetic field coupling the primary coil to the sense coil when the primary coil is inductively coupled to the secondary coil.

30. The antenna assembly of claim 29, further comprising a temperature sensor adapted to determine a temperature of at least a portion of the antenna assembly.

31. The antenna assembly of claim 30, further comprising an auxiliary interface coupled to the temperature sensor, the auxiliary interface having at least one data line for communicating data.

32. The antenna assembly of claim 29, further comprising a storage device adapted to store data describing the antenna assembly.

33. The antenna assembly of claim 29, wherein the sense coil interface is adapted to provide a signal indicating a frequency at which the IMD will communicate with the antenna assembly.

34. The antenna assembly of claim 29, further comprising a primary coil interface adapted to couple the primary coil to at least one additional primary coil of another antenna assembly.

35. The antenna assembly of claim 29, wherein the sense coil interface is adapted to couple the sense coil to at least one additional sense coil of another antenna assembly.

36. The method of claim 35, further comprising selecting a maximum voltage amplitude that may be attained across the sense coil when recharging the rechargeable power source.

37. The method of claim 36, wherein selecting a maximum voltage amplitude is performed programmably.

38. The antenna assembly of claim 29, wherein the coil configuration of the primary coil is selected from the multiple possible coil configurations based on a type of an IMD to be recharged.

39. The antenna assembly of claim 29, wherein the sense coil interface is adapted to drive sense coils of multiple different types of configurations.

40. A method of transcutaneously recharging a rechargeable power source of an implantable medical device (IMD), comprising:
receiving, by a recharging device, a primary coil that is removably coupleable to the recharging device, wherein the primary coil may be any one of multiple types of primary coils; and
receiving, by the recharging device, a sense coil that is removably coupleable to the recharging device, wherein the sense coil is configured to maintain a given ratio between voltage across the primary coil and voltage across the sense coil when the primary coil is recharging the rechargeable power source, wherein the sense coil has a coil configuration that is determined based on the type of the primary coil.

41. The method of claim 40, further comprising automatically determining a resonant frequency for driving the primary coil during recharging the rechargeable power source.

42. The method of claim 40, wherein removably coupling a sense coil to the recharging device includes selecting at least one of a number of turns, size and shape of the sense coil.

43. The method of claim 40, further comprising:
removably coupling multiple primary coils to the recharging device; and
for each of the multiple primary coils, removably coupling a corresponding sense coil to the recharging device, the corresponding sense coil being configured to maintain a given ratio between voltage across the respective primary coil and voltage across the sense coil when the primary coil is recharging the rechargeable power source.

44. The method of claim 40, wherein at least one of the primary coil and the sense coil is removably coupleable to a connector of the recharging device.

45. The method of claim 40, further comprising driving, via the recharging device, a primary coil that is any selected one of the multiple types of primary coils while the sense coil maintains a given ratio between voltage across the primary coil and voltage across the sense coil.

46. The method of claim 40, wherein receiving, by a recharging device, a primary coil comprises receiving, by a recharging device, a primary coil selected based on a type of an IMD that is to be recharged.

47. The method of claim 40, wherein the IMD is of a first type, and further comprising:
decoupling, from the recharging device, the primary coil and the sense coil;
receiving, by a recharging device, a second primary coil of a type that is different from the type of the primary coil; and
receiving, by the recharging device, a second sense coil, wherein the second sense coil is configured to maintain a given ratio between voltage across the second primary coil and voltage across the second sense coil when the second primary coil is recharging a rechargeable power source of an IMD of second type different from the first type.

48. A system, comprising:
an implantable medical device (IMD);
an external device adapted to transmit electromagnetic energy to the IMD; and
an antenna assembly physically removably coupled to the external device, the antenna assembly having a primary coil and a sense coil having a configuration that is selected based on a configuration of the primary coil, the sense coil adapted to prevent voltage across the primary coil from exceeding a selected maximum voltage amplitude;

wherein the primary coil may be any selectable one of multiple configurations, and wherein the external device is adapted to drive any of the multiple configurations.

49. The system of claim 48, wherein the IMD comprises a secondary coil and a rechargeable power source, wherein the secondary coil is adapted to transfer the electromagnetic energy to the rechargeable power source.

50. The system of claim 48, wherein the IMD comprises a communication module adapted to provide feedback to the external device indicating status concerning transmission of the electromagnetic energy to the IMD.

51. The system of claim 48, wherein the external device comprises a voltage limiting circuit adapted to select the maximum voltage amplitude based on a selected magnetic field strength.

52. The system of claim 48, wherein the maximum voltage amplitude is programmable.

53. The system of claim 48, wherein the external device comprises a rechargeable power source and a circuit configured to return energy to the rechargeable power source when the voltage across the primary coil reaches the maximum voltage amplitude.

54. The system of claim 48, wherein the external device further comprises a modulation circuit adapted to provide the electromagnetic energy and a compare circuit adapted to limit energy transferred from the modulation circuit to the primary coil when the voltage across the primary coil reaches the maximum voltage amplitude.

55. The system of claim 48, wherein the device comprises a modulation circuit adapted to automatically determine the resonant frequency of the antenna assembly.

56. The system of claim 48, wherein the external device comprises a connector configured to receive the antenna assembly.

57. The system of claim 48, wherein the primary coil has a selectable configuration, the selectable configuration comprising at least one of a selectable electrical property and a selectable magnetic property.

* * * * *